United States Patent

Meyer et al.

[11] Patent Number: 5,817,873
[45] Date of Patent: Oct. 6, 1998

[54] POLYIODINATED COMPOUNDS, THEIR PREPARATION AND THEIR USE AS CONTRAST MEDIA FOR RADIOLOGY

[75] Inventors: Dominique Meyer, Saint Maur; Soizic le Greneur, Bures sur Yvette; Gaël le Lem, Suresnes; Christian Simonot, Paris; Catherine Chambon, Igny, all of France

[73] Assignee: Guerbet S.A., Villepinte, France

[21] Appl. No.: 331,544

[22] PCT Filed: Mar. 21, 1994

[86] PCT No.: PCT/FR94/00305

§ 371 Date: Nov. 1, 1994

§ 102(e) Date: Nov. 1, 1994

[87] PCT Pub. No.: WO94/21600

PCT Pub. Date: Sep. 29, 1994

[30] Foreign Application Priority Data

Mar. 22, 1993 [FR] France ................................ 93 03269

[51] Int. Cl.⁶ .................................................. C07C 237/46
[52] U.S. Cl. .......................... 564/158; 564/153; 564/156; 424/9.44; 424/9.452
[58] Field of Search ...................... 564/156, 153, 564/158, 152, 155, 157; 424/9.44, 9.452

[56] References Cited

FOREIGN PATENT DOCUMENTS 0115771   8/1984   European Pat. Off. .
0271180B1 5/1993   European Pat. Off. .

OTHER PUBLICATIONS

Article entitled: "Polymers with Controlled Molecular Architecture: Control of Surface Functionality in the Synthesis of Dendritic Hyperbranched Macromolecules using the Convergent Approach"; J. Chem. Soc. Perkin Trans. 1991; pp. 1059–1076; Karen L. Wooley, Craig J. Hawker and Jean M. J. Frechet.

Article entitled: Starburst Dendrimers: Molecular–Level Control of Size, Shape, Surface Chemistry, Topology, and Flexibility from Atoms to Macroscopic Matter; Angew. Chem. Int. Ed. Engl. 29 (1990) 138–175; pp. 138–175; Donald A. Tomalia, Adel M. Naylor, and William A. Goddard III.

*Primary Examiner*—Brian M. Burn
*Attorney, Agent, or Firm*—Jacobson, Price, Holman & Stern, PLLC

[57] ABSTRACT

The present invention relates to polyiodinated compounds with a single molecular weight having a molecular concentration of iodine of greater than approximately 20% by weight, and in particular greater than approximately 30% by weight, containing at least 9 iodine atoms and having a molecular weight above 2000 and below approximately 50,000, and in particular above 2000 and below approximately 20,000, said compounds possessing either a zero overall electrical charge or at least two anionic charges, and persisting in the vascular compartment at a value equal to at least approximately 30% by weight of the injected dose in a subject five minutes after intravascular administration in the said subject.

18 Claims, No Drawings

POLYIODINATED COMPOUNDS, THEIR PREPARATION AND THEIR USE AS CONTRAST MEDIA FOR RADIOLOGY

The present invention relates to compounds which can be used as contrast media for X-ray radiology.

The present invention relates more especially to compounds which can be used as contrast media displaying a long residence in the vascular compartment.

There is still a need for this type of product at the present time.

In effect, the traditional ionic or nonionic media customarily used, such as triiodinated derivatives of isophthalic acid, are very rapidly extravasated. The time available for obtaining an image of the vascular compartment of sufficient quality is thus very short.

To remedy this drawback, it has been proposed to repeat the injections of traditional contrast media. This approach entails, however, an increase in doses and a higher risk of adverse side effects. It also results in a greater cost of examinations of the vascular compartment.

Contrast media displaying a long residence in the vascular compartment for X-ray radiology have, moreover, been proposed; they are all based on the principle of attachment of a number of iodinated molecules to a high molecular weight polymer.

In this way, the contrast medium is excreted slowly by glomerular filtration and remains confined in the vascular compartment, at least for a certain time.

There may be mentioned, in this connection, EP-354 836 and EP-344,202 describing compounds possessing a dextran type backbone onto which iodinated phenyl groups are grafted, EP 436,316 describing compounds with polyacrylamide backbone onto which iodinated phenyl groups are grafted or alternatively U.S. Pat. No. 5,019,370 describing compounds having a polyacrylate or polyamide backbone.

The major drawback of the products of the prior art lies, however, in the polydispersity of the molecular weight of the polymers used, such as dextran or polylyine, or resulting from the copolymerization of the acrylamide type monomers used.

This polydispersity has several drawbacks: in the first place, the low molecular weight components of the iodinated polymer are excreted rapidly and no longer contribute to the concentration which is useful for obtaining the vascular image.

In addition, extravasation of the low molecular weight polymers into the interstitial compartment decreases the contrast at the interface between the vascular and interstitial compartments, and results in an image of insufficient quality.

Lastly, the high molecular weight components of the iodinated polymer are eliminated only very slowly via the kidneys or by uptake by the reticuloendothelial system, and may generate undesirable anaphylactoid reactions.

Hence the compounds proposed hitherto do not permit the confinement of a contrast medium in the vascular compartment, or its biocompatibility, to be controlled in a precise manner.

Polyiodinated compounds comprising up to 3 phenyl rings are, moreover, known from FR 2,272,640.

These compounds are not, however, described as being capable of displaying a long residence in the vascular compartment.

The objective of the present invention is to provide compounds which can be used as contrast media for X-ray radiology which do not possess the drawbacks of the compounds of the prior art while displaying a good residence time in the vascular compartment.

The subject of the invention is polyiodinated compounds with a single molecular weight having a molecular concentration of iodine of greater than approximately 20% by weight, and in particular greater than approximately 30% by weight, containing at least 9 iodine atoms and having a molecular weight above 2000 and below approximately 50,000, and in particular above 2000 and below approximately 20,000, characterized in that they have either a zero overall electrical charge or at least two anionic charges, and in that they persist in the vascular compartment at a value equal to at least approximately 30% by weight of the injected dose in a subject five minutes after intravascular administration in the said subject.

Single molecular weight is understood, in the context of the present invention, to mean a molecular weight which is not defined as an average of the different molecular weights present for the same compound, as opposed to the dispersity of the molecular weights of the polymers of the prior art mentioned hereinbefore.

In other words, a compound according to the invention, possessing a single molecular weight, is understood to mean a product possessing an index of polydispersity equal to 1.

The subject of the invention is, in particular, polyiodinated compounds which are characterized in that they contain at least one group of formula

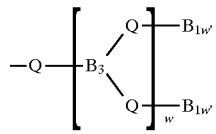

with $w=\Sigma_0^n 2^n$ and $w'=2^n$, n representing an integer from 0 to 4, the groups Q, which may be identical to or different from one another, represent a single bond or a group selected from:

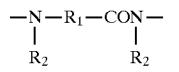

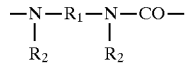

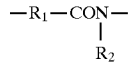

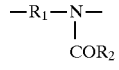

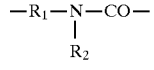

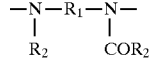

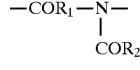

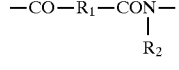

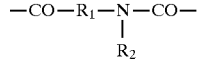

-continued

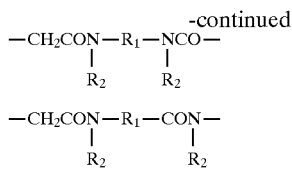

in which:
R₁ is selected from an alkylene group having a linear or branched $C_1$–$C_{10}$ chain, a hydroxy- or polyhydroxyalkylene group having a linear or branched $C_1$–$C_{10}$ chain, a ($C_1$–$C_5$ alkoxy)alkylene group having a linear or branched $C_1$–$C_{10}$ chain, a hydroxy- or polyhydroxy ($C_1$–$C_5$ alkoxy)alkylene group having a linear or branched chain, and a single bond, and the groups $R_2$, which may be identical or different, are selected from H, an alkyl group having a linear or branched $C_1$–$C_{10}$ chain, a hydroxy- or polyhydroxyalkyl group having a linear or branched $C_1$–$C_{10}$ chain, a ($C_1$–$C_5$ alkoxy)alkyl group having a linear or branched $C_1$–$C_{10}$ chain and a hydroxy- or polyhydroxy ($C_1$–$C_5$ alkoxy)alkyl group having a linear or branched chain;

the groups $B_1$, which may be identical to or different from one another, represent the residue of an aromatic group containing at least three iodine atoms and are preferably selected from the groups of formulae:

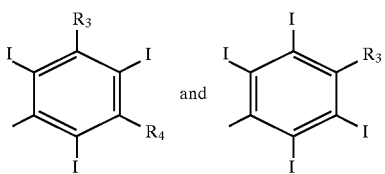

in which
$R_3$ is selected from:
a group —COO⁻ M⁺ with M⁺ representing H⁺ or a physiologically acceptable cation of an organic or inorganic base,
a group

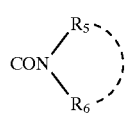

and
a group

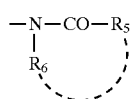

in which
$R_5$ and $R_6$, which may be identical to or different from one another, represent H or a linear or branched $C_1$–$C_{10}$ alkyl, linear or branched $C_1$–$C_{10}$ hydroxy- or polyhydroxyalkyl, linear or branched $C_1$–$C_{10}$ ($C_1$–$C_5$ alkoxy)alkyl or linear or branched $C_1$–$C_{10}$ hydroxy- or polyhydroxy($C_1$–$C_5$ alkoxy)alkyl group, a $C_1$–$C_6$ alkyl group substituted with one or more (preferably from 1 to 9) hydroxy- or polyhydroxyalkoxy group(s) or a $C_1$–$C_6$ hydroxy- or polyhydroxyalkyl group substituted with one or more (preferably from 1 to 9) $C_1$–$C_{10}$ hydroxy- or polyhydroxyalkoxy group(s)

or $R_5$ and $R_6$ together form a $C_4$–$C_8$ alkylene, $C_4$–$C_8$ hydroxyalkylene or $C_4$–$C_8$ polyhydroxyalkylene group having a linear or branched chain which is optionally interrupted by one or more atoms chosen from S, O, P and N, so that $R_5$ and $R_6$, with the nitrogen atom to which they are linked, form a 5- to 12-membered nitrogenous heterocycle optionally substituted with one or more hydroxyl groups or $C_1$–$C_4$ hydroxy- or polyhydroxyalkyl groups having a linear or branched chain and optionally containing one or more additional hetero atoms selected from S, O, P and N, $R_4$ represents a group selected from $R_3$ and a group of formula Q—$B_4$, Q being as defined above and $B_4$ representing a group:

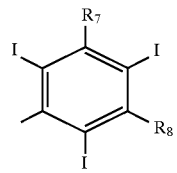

in which $R_7$ and $R_8$, which may be identical to or different from one another, represent $R_3$, the groups $B_3$, which may be identical to or different from one another, are selected from:

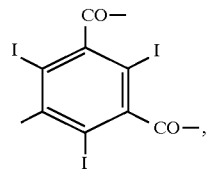

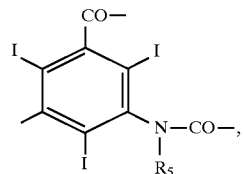

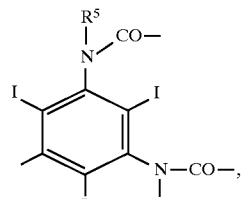

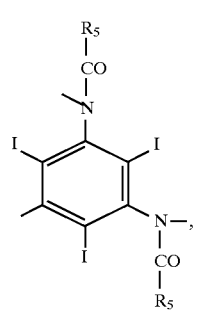

and

-continued

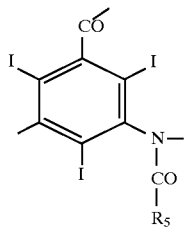

in which $R_5$ has the meanings given above.

In a further aspect, the invention relates more especially to polyiodinated compounds of generic formula I:

$$A\text{-}(X)_m \quad (I)$$

in which:

A represents the residue of a polyfunctional molecule containing either a central tri- or tetrasubstituted carbon atom and/or at least one aromatic or non-aromatic carbocycle optionally containing one or more iodine atoms, or at least one aromatic or non-aromatic heterocycle containing from 1 to 4 hetero atoms chosen from O, S, N and P, to which molecule are bound m groups X via m bonds or via m groups selected from —C—, $$-CO-, -\underset{R_5}{N}-, -O-, \diagdown NCOR_5;$$

—O—, >$NCOR_5$;

the groups X, which may be identical to or different from one another, represent the groups:

—Q—$B_1$ (A),

—Q—$A_1$—(Q—$B_1$)$_{m'}$ (B), m' representing from 2 to 11; or

—Q—$B_2$—Q—$B_1$ (C)

or the groups X, which may be identical or different, represent:

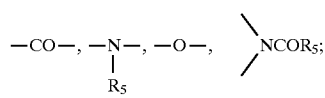 (D)

with w, w', Q, $B_1$ and $B_3$ as defined above, m represents an integer from 3 to 12 when X represents the groups (A), (B) or (C), and from 2 to 12 when X represents the group (D), $A_1$ is selected from the groups A, with the proviso that at least one group —CO—,

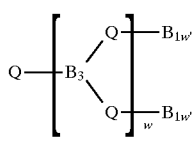

or

is replaced by a single bond, $B_2$ is selected from the groups:

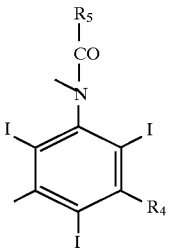

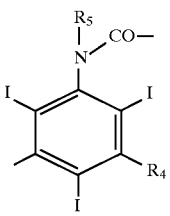

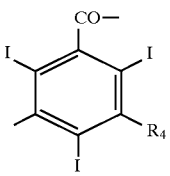

in which $R_4$ and $R_5$ have the meanings given above; with the proviso that the said compounds contain a zero overall electrical charge or at least two anionic charges when $A—(—X)_m = A—(—QB_1)_3$, and that said compounds have a molecular weight above 2000 and below approximately 50,000.

Advantageously, in a further aspect, the invention relates to compounds of generic formula I as described above, in which:

A represents a residue of a polyfunctional molecule containing a central carbon atom, selected from a residue of formula $CR_9(R_{10}—Y—)_3—$ in which $R_9$ represents a hydrogen atom, a $C_1$–$C_6$ alkyl or $C_5$–$C_{10}$ aryl group or a group ($R_{10}$—Y), $R_{10}$ being chosen from a $C_1$–$C_6$ alkylene, $C_5$–$C_{10}$ arylene, ($C_1$–$C_{10}$ alkyl)($C_5$–$C_{10}$ arylene) and ($C_5$–$C_{10}$ aryl)($C_1$–$C_6$ alkylene) group, it being possible for the alkylene groups to be optionally interrupted by one or more oxygen atoms, and the alkyl, alkylene, aryl or arylene groups being optionally substituted with one or more OH groups, Y being selected from an —O—, —CO— group or a group

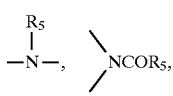

>$NCOR_5$, $R_5$ being as defined above, or A represents an optionally polycyclic $C_5$ to $C_{12}$ cycloalkane residue optionally containing from 1 to 6 iodine atoms and from 2 to 12 identical or different substituents of formula —$R_{11}$—$(Y)_q$, q representing an integer from 1 to 3, $R_{11}$ being a single bond or a linear or branched $C_1$–$C_6$ alkylene group optionally substituted with one or more OH groups and/or interrupted by one or more oxygen atoms, and Y being as defined above, or A represents a monocyclic or bicyclic $C_5$–$C_{12}$ aromatic hydrocarbon residue optionally containing from 3 to 6 iodine atoms and optionally containing one or more substituents selected from OH, $NH_2$, $C_1$–$C_6$ alkyl, $C_1$–$C_6$ hydroxy- or polyhydroxyalkyl, COOH, $COOR_{12}$, —CO—$NHR_{12}$ or —$NR_6COR_5$, $R_{12}$ representing a $C_1$–$C_4$ alkyl group and containing from 2 to 12 substituents of formula —$R_{11}$—(—Y—)$_q$, q and $R_{11}$ being as defined above and Y representing a group selected from —O—, —CO—,

or A represents an optionally aromatic monocyclic or bicyclic heterocyclic residue containing from 5 to 10 ring-members including 1 to 4 hetero atoms selected from O, S, N and P, optionally substituted with 3 to 6 identical or different substituents selected from =O, and containing from 3 to 12 substituents of formula —$R_{11}$—(—Y—)$_q$, Y and q being as defined above;

or A represents an optionally cyclic residue containing from 2 to 18 aromatic or heterocyclic ring-systems as defined above, linked to one another through groups —$R_{11}$—, —$OR_{11}$—, $R_{11}$ being as defined above, this residue containing from 3 to 12 substituents of formula —$R_{11}$—(—Y—)$_q$, $R_{11}$, Y and q being as defined above, the groups X, which may be identical or different, represent the groups:

 (A)

 (B)

m' representing from 2 to 11; or

 (C)

or

X represents a group:

 (D)

and w=$\sum_0^n 2^n$ and w'=$2^n$, n representing an integer from 0 to 4, m represents an integer from 3 to 12 when X represents the groups (A), (B) or (C), and from 2 to 12 when X represents the group (D), the groups Q, which may be identical to or different from one another, represent a single bond or a group selected from:

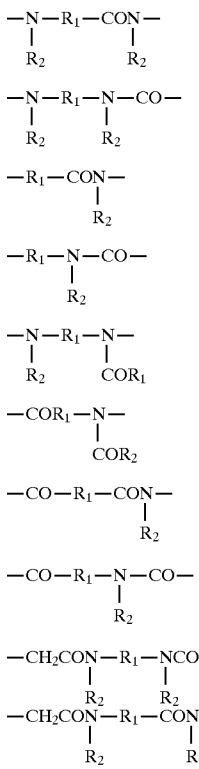

in which:

$R_1$ is selected from a single bond, an alkylene group having a linear or branched $C_1$–$C_{10}$ chain, a hydroxy- or polyhydroxyalkylene group having a linear or branched $C_1$–$C_{10}$ chain, a ($C_1$–$C_5$ alkoxy)alkylene group having a linear or branched $C_1$–$C_{10}$ chain and a hydroxy- or polyhydroxy($C_1$–$C_5$ alkoxy)alkylene group having a linear or branched chain, the alkylene chain being optionally interrupted by one or more oxygen atoms, in particular 1 to 4, $R_2$ is selected from H, an alkyl group having a linear or branched $C_1$–$C_{10}$ chain, a hydroxy- or polyhydroxyalkyl group having a linear or branched $C_1$–$C_{10}$ chain, a ($C_1$–$C_5$ alkoxy)alkyl group having a linear or branched $C_1$–$C_{10}$ chain and a hydroxy- or polyhydroxy ($C_1$–$C_5$ alkoxy)alkyl group having a linear or branched chain;

$A_1$ is selected from the groups A, with the proviso that at least one group —CO—,

or >$NCOR_5$ is replaced by a single bond;

the groups $B_1$, which may be identical to or different from one another, represent the residue of an aromatic group containing at least three iodine atoms and are preferably selected from the groups of formula:

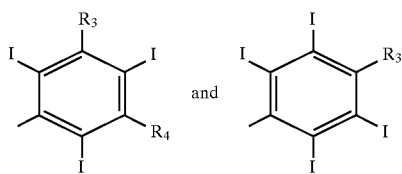

in which

R₃ is selected from:

a group —COO⁻ M⁺ with M⁺ representing H⁺ or a physiologically acceptable cation of an organic or inorganic base, in particular Na⁺, Ca⁺, Mg⁺, glucamine, methylglucamine, lysine or arginine, a group

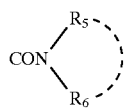

and a group

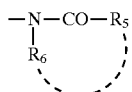

in which $R_5$ and $R_6$, which may be identical to or different from one another, represent H or a linear or branched $C_1$–$C_{10}$ alkyl, linear or branched $C_1$–$C_{10}$ hydroxy- or polyhydroxyalkyl, linear or branched $C_1$–$C_{10}$ ($C_1$–$C_5$ alkoxy)alkyl or linear or branched $C_1$–$C_{10}$ hydroxy- or polyhydroxy($C_1$–$C_5$ alkoxy)alkyl group, or $R_5$ and $R_6$ together form a $C_4$–$C_8$ alkylene, $C_4$–$C_8$ hydroxyalkylene or $C_4$–$C_8$ polyhydroxyalkylene group having a linear or branched chain which is optionally interrupted by one or more atoms selected from S, O, P and N, so that $R_5$ and $R_6$, with the nitrogen atom to which they are linked, form a 5- to 12-membered nitrogenous heterocycle optionally substituted with one or more hydroxyl groups or $C_1$–$C_4$ hydroxy- or polyhydroxyalkyl groups having a linear or branched chain and optionally containing one or more additional hetero atoms selected from S, O, P and N, $R_4$ represents a group selected from $R_3$ and the groups of formula Q—$B_4$, Q being as defined above and $B_4$ representing a group

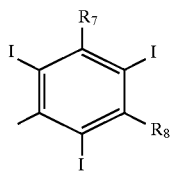

in which $R_7$ and $R_8$, which may be identical to or different from one another, represent $R_3$ as defined above, $B_2$ is selected from the groups:

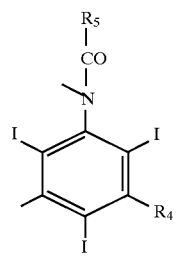

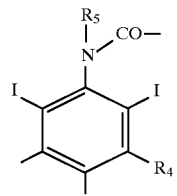

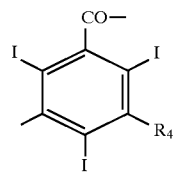

in which $R_4$ and $R_5$ have the meanings given above; the groups $B_3$, which may be identical to or different from one another, are selected from:

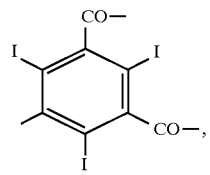 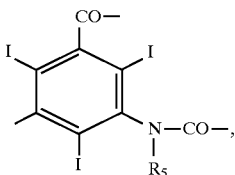

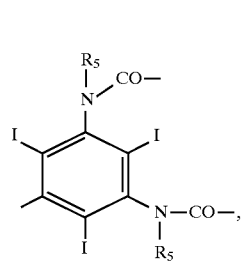 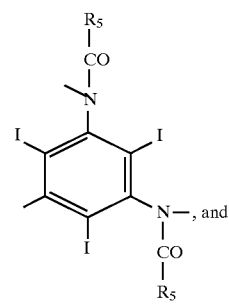

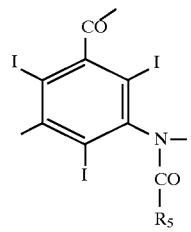

in which $R_5$ has the meaning given above, with the proviso that the said compounds contain a zero overall electrical charge or at least two anionic charges when A—(—X)$_m$= A—(—QB₁)₃, and that the said compounds possess a molecular weight above 2000 and below approximately 50,000.

The products of the invention in which the group X is a group (D) correspond, for example, to the formula below:

with n=2, w=7 and w'=4, the following compound is obtained:

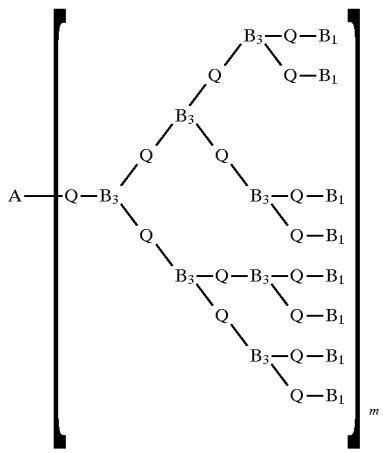

It is self-evident that the invention encompasses not only compounds of formula (I) in the form of a racemic mixture, but also stereoisomers such as enantiomers, diastereoisomers, atropoisomers and syn-anti, endoexo and E-Z isomers, associated with the presence of asymmetric carbon atoms and/or with obstructions to rotation due to the steric hindrance brought about by the iodine atoms and/or the substituents R of the compounds of the invention.

Among the different types of group A, there may be mentioned:

A) a residue of formula $C(R_{10}-y-)_4$, $R_{10}$ representing a group $(CH_2)_{n_1}$ with $n_1=1$ to 5, optionally interrupted by 1 to 4 oxygen atoms, in particular a methylene group or a —$CH_2$—O—$CH_2$— or —$CH_2$—O—$(CH_2)_2$, or a phenylene or phenylmethylene group, and Y being as defined above, and more especially the following groups:

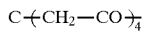

described in J. Chem. Soc. (1922), 1638;

$C-(CH_2-O-CH_2-CH_2-CO)_4-;$

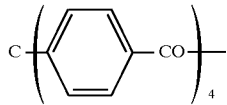

described in Angew. Chem. Int. Ed. Eng., 25, 1097, 1986;

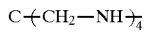

described in U.S. Pat. No. 3,994,972
J.C.S., 1938, 1588–1595

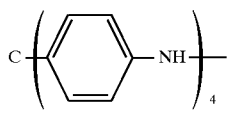

described in F. A. Neugebauer, Chem. Ber., 109, 2389, 1976

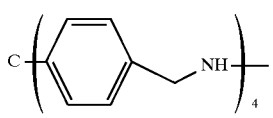

described in Angew. Chem. Int. Ed. Engl. 25, 1097, 1986 and JACS, 101, 2728, 1979.

B) a cycloalkane residue selected from cyclohexane and adamantane, substituted with 3 or 4 substituents $R_{11}-(Y-)_q$ as defined above, and in particular the following groups:

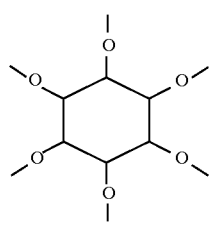

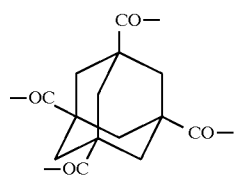

described in Newkome, J. Org. Chem., 57, 358, 1992;

C) a phenyl group optionally substituted with 3 to 4 iodine atoms or a biphenyl group optionally substituted with 4 to 6 iodine atoms and optionally containing from 3 to 6 substituents of formula —$R_{11}$—(Y—)$_q$, $R_{11}$ and Y being as defined above, in particular the following groups:

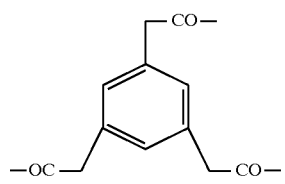

J.A.C.S. (1954) 76, 6196

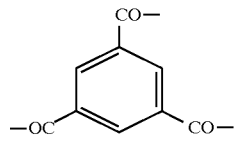

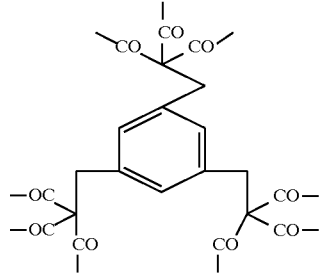

J. Org. Chem. 50 (1985) 2001
J. Am. Chem. Soc. 108 (1986) 849
J. Chem. Soc. Chem. Comm. 1986, 752

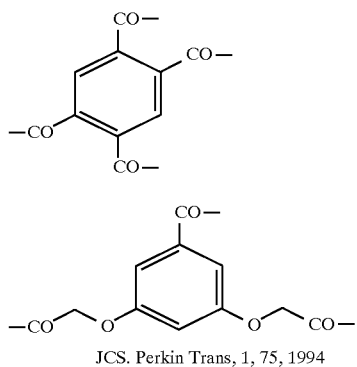

JCS. Perkin Trans, 1, 75, 1994

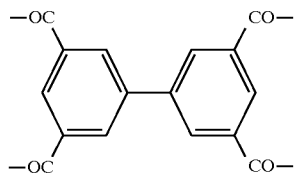

N. Raymond, J. Am. Chem. Soc., 101, 2728, 1979

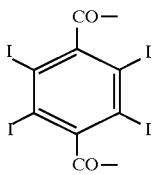

C.E. Castro, J. Am. Chem. Soc. 80, 2322, 1958

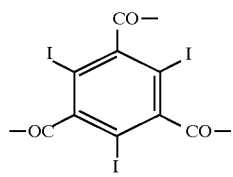

DE 1 066 707
US 2 247 880

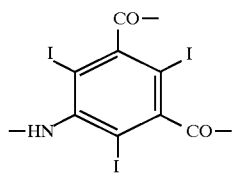

US 5 047 228

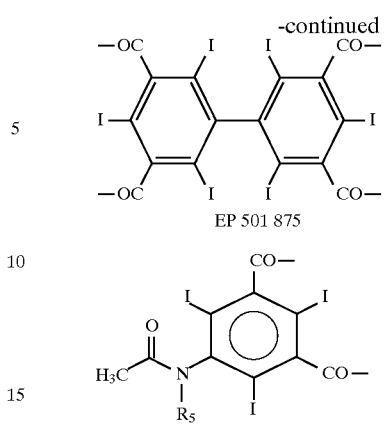

FR 2 053 037
FR 2 457 104

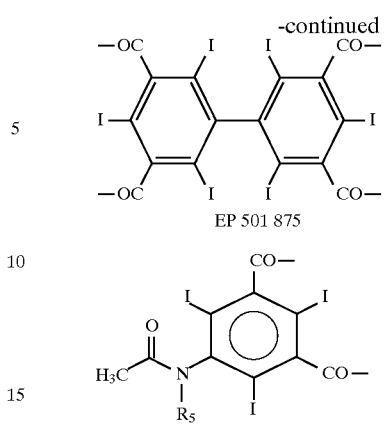

EP 501 875

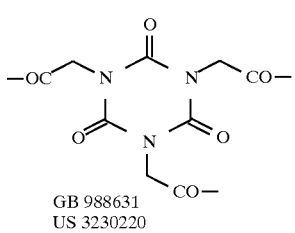

Sovak, M. Radio Contrast Agents,
Berlin, New York, Springer, 1984

D) a heterocyclic residue consisting of a 2,4,6-trioxo-1,3,5-triazine group substituted on the nitrogen atoms with 3 substituents of formula —$R_{11}$—$(Y_1$—$)_q$ as defined above, and in particular the groups:

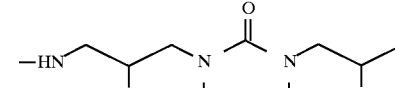

GB 988631
US 3230220

E) a macrocycle containing 6 to 8 phenyl residues each substituted with one or more substituents selected from OH, $NH_2$, $C_1$–$C_6$ alkyl, $C_1$–$C_6$ hydroxy- or polyhydroxyalkyl, COOH, $COOR_{12}$, —CO—$NHR_{12}$— and —$NR_6COR_5$, $R_{12}$ representing a $C_1$–$C_4$ alkyl group, and one or more groups of the formula $R_{11}$—(Y—) q as defined above with q=1, the phenyl residues being linked to one another through a methylene group, or a cyclodextrin containing 6 to 8 glucosyl residues linked to one another through a glycosidic linkage, one or more OH groups of the said glucosyl residues being optionally substituted with a carboxymethyl residue, one or more OH groups of the said glucosyl residues being replaced by an —O— group, or a macrocycle containing more than one nitrogen, such as 1,4,7,10-tetraazacyclododecane or 1-oxo-4,7,10-triazacyclododecane, or a derivative of a polyaminocarboxylic acid, such as DOTA (1,4,7,10-tetraazacyclododecanetetraacetic acid) or DO3A (1,4,7,10-tetraazacyclododecanetriacetic acid), in particular the residues:

calixarene derivatives having eight rings, of formula:

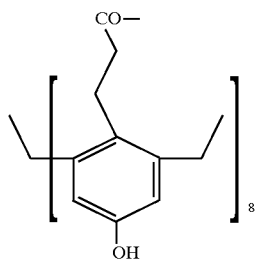

J.A.C.S. (1988) 110
6153–62 the residues derived from α-, β- and γ-cyclodextrins and carboxymethyl-α-, -β- and -γ-cyclodextrins (U.S. Pat. No. 4,247,535, Carbohydr. Res. 63, 13 (1978)) by elimination of one or more H atoms on the glucosyl residues;

DOTA, DO3A.

The group B, is advantageously selected from:

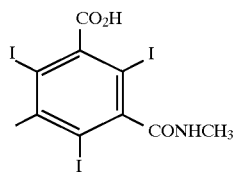

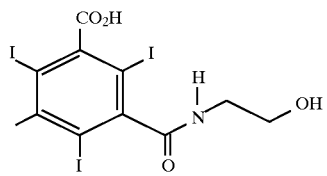

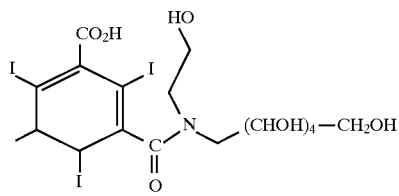

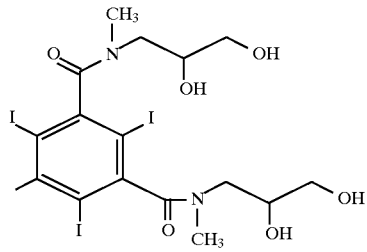

CA 1 129 438

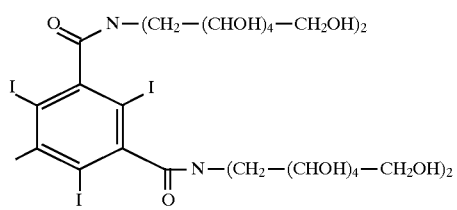

The group $B_3$ is advantageously selected from:

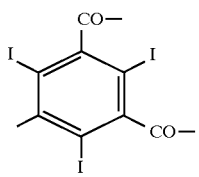

The group Q is advantageously selected from:

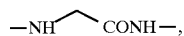

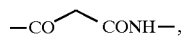

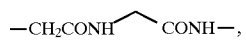

—$(CH_2)_r$CONH—, and

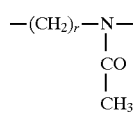

r being an integer from 1 to 5.

$R_3$ is advantageously selected from:

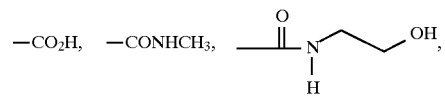

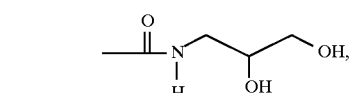

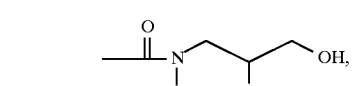

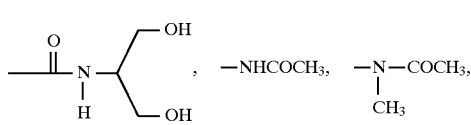

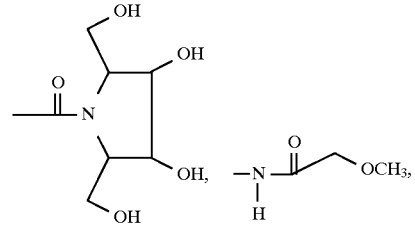

-continued

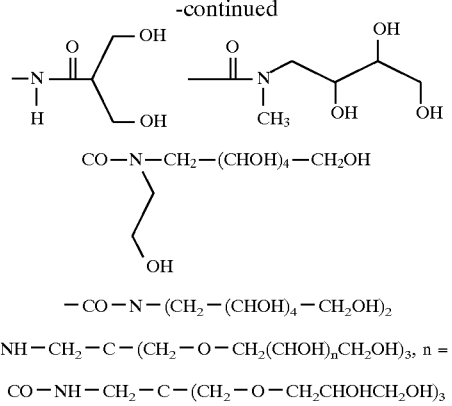

CO—N—CH$_2$—(CHOH)$_4$—CH$_2$OH
           |
          (CH$_2$)
           |
           OH

—CO—N—(CH$_2$—(CHOH)$_4$—CH$_2$OH)$_2$

CO—NH—CH$_2$—C—(CH$_2$—O—CH$_2$(CHOH)$_n$CH$_2$OH)$_3$, n = 1 to 4

CO—NH—CH$_2$—C—(CH$_2$—O—CH$_2$CHOHCH$_2$OH)$_3$ $R_4$ is advantageously selected from the groups $R_3$ and a group of formula —Q—$B_4$, Q being as defined above and $B_4$ representing a group of formula:

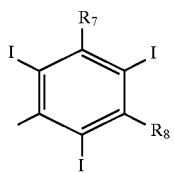

$R_7$ $R_8$ having the same meanings as $R_3$.

A first group of preferred compounds according to the invention is represented by the compounds of the generic formula II:

A—(—Q—$B_1$)$_3$ (II)

A and $B_1$ being as defined above and Q represents a group:

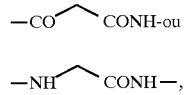

A second group of preferred compounds according to the invention is represented by the compounds of the generic formula III:

A—[—Q—$A_1$—(Q—$B_1$)$_2$]$_3$ (III)

in which:

A and $A_1$ are as defined above,

Q represents a group

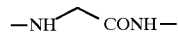

$A_1$ represents a group

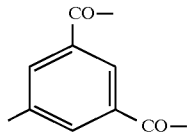

and $B_1$ represents a group

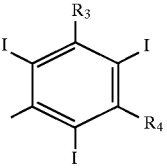

$R_3$ and $R_4$ being as defined above.

A third group of preferred compounds according to the invention is represented by the compounds of the general formula IV:

A—(—Q—$B_2$—Q—$B_1$)$_3$ (IV)

in which A and $B_1$ are as defined above,

Q represents a group

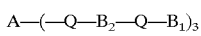

and $B_2$ represents a group

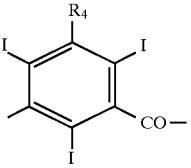

$R_4$ being as defined above.

A fourth group of preferred compounds according to the invention is represented by the compounds of general formula V:

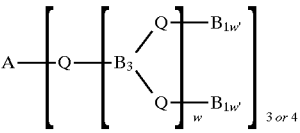

$w=\Sigma_0^n 2^n$ and $w'=2^n$ (n representing an integer from 0 to 4)

in which formula A and $B_1$ are as defined above,

Q preferably represents a group

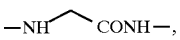

and $B_3$ represents a group:

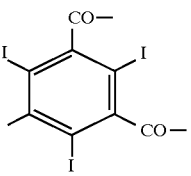

These compounds have a branched structure, each group $B_3$ being linked to three groups Q. The degree of branching (n) can range up to 4. Thus, the structure of these compounds obeys a geometric progression of common ratio 2 as defined above.

Preferred compounds of the invention are also those in which the groups X differ from one another. For example, a compound of the invention is that which has the formula below:

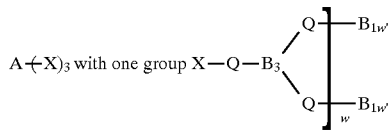

and two groups X=—Q—B.

The following compound is thereby obtained:

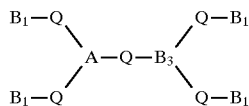

With A=

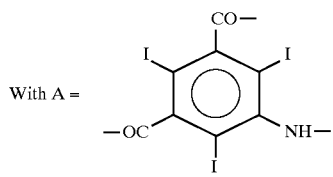

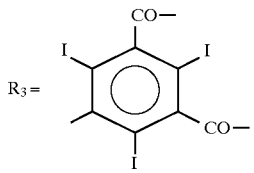

and

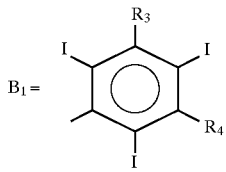

the following compound is obtained:

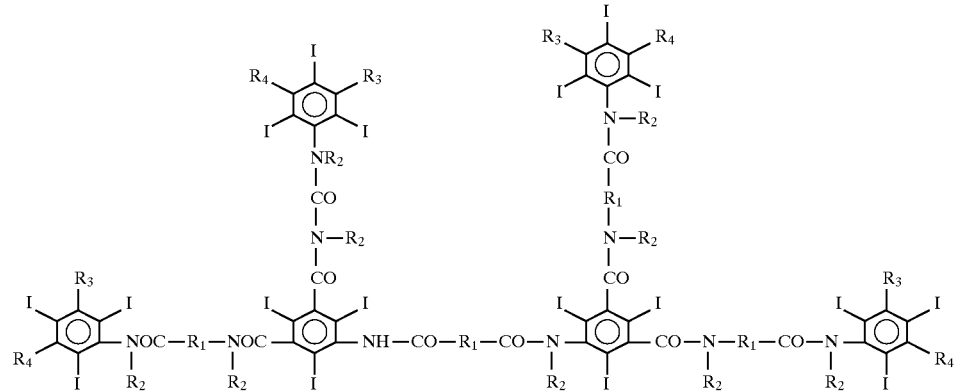

Preferred groups of compounds in which $M^+$ has one of the definitions stated above, have the following general formulae:

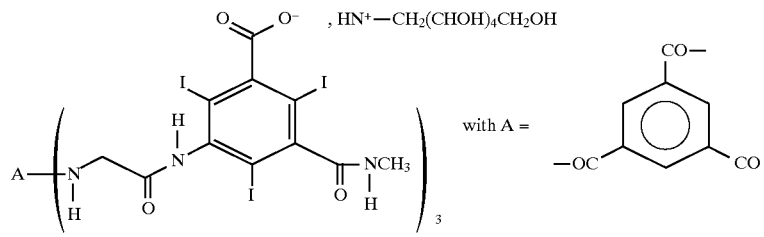

-continued
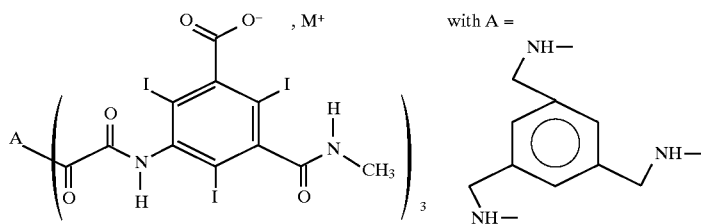
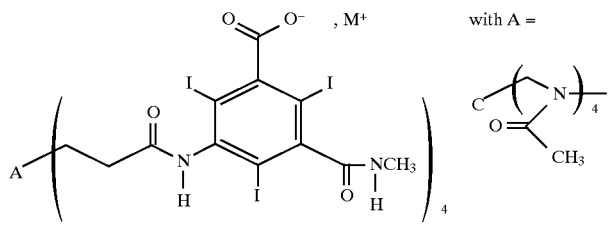
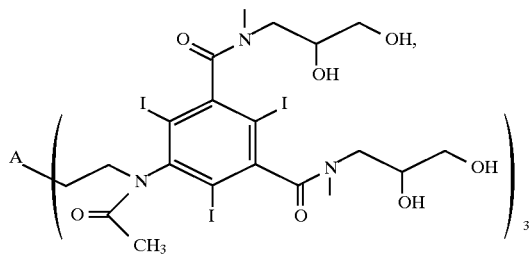
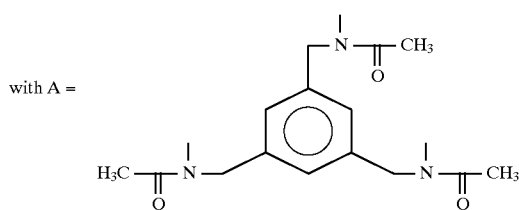
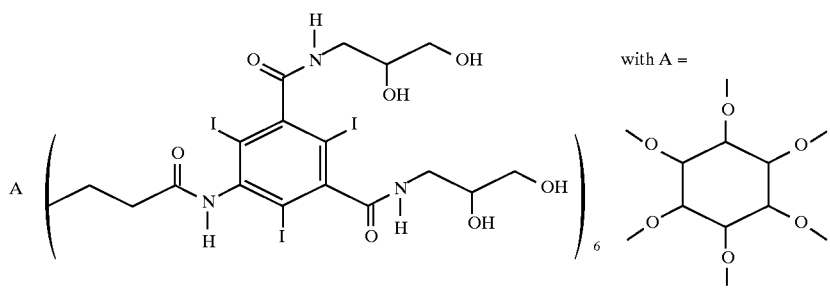
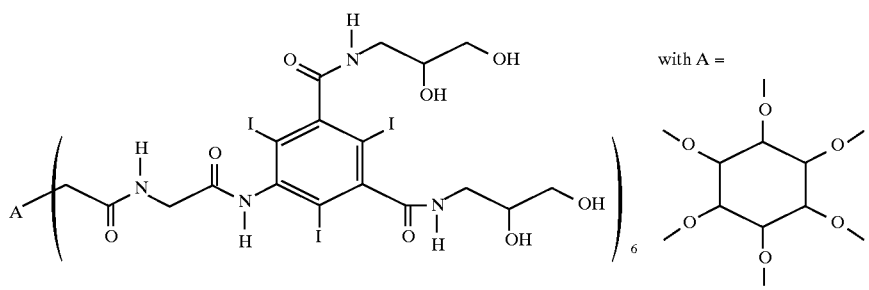

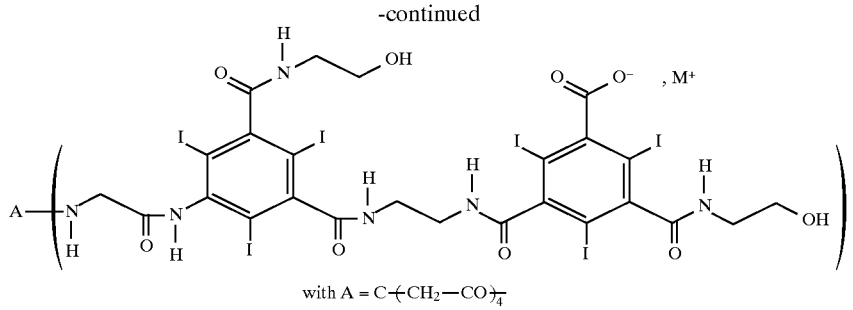
with A = C⁻(CH₂—CO)₄⁻
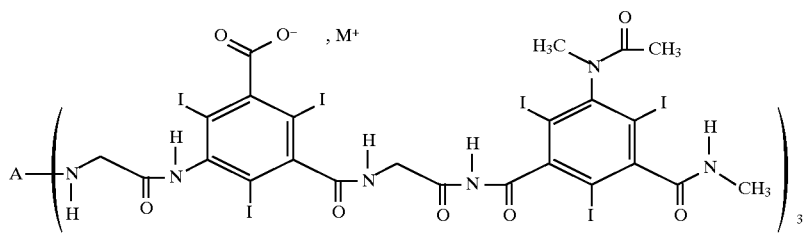
with A = 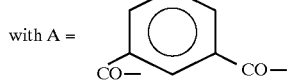
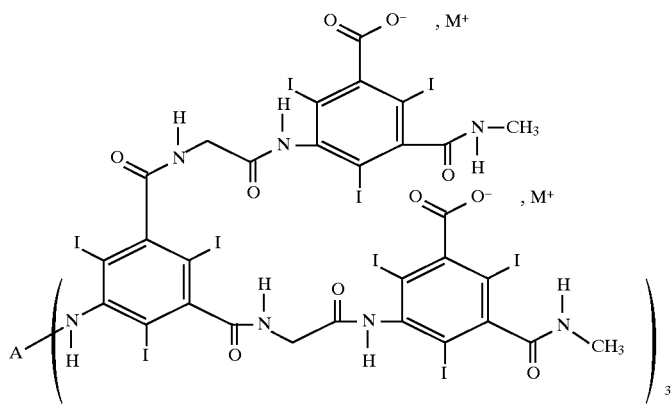
with A = 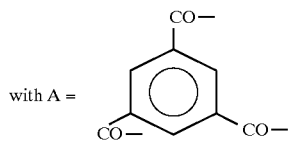
Among preferred compounds, the following compounds may be mentioned:
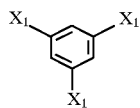
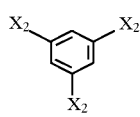
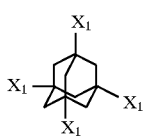
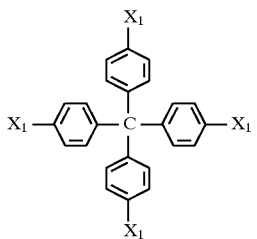

-continued

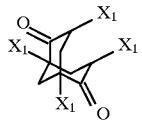

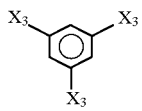

with:

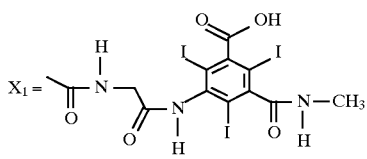

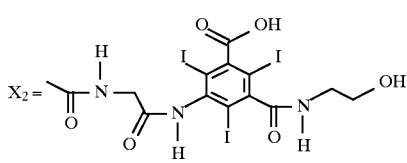

X₃ =

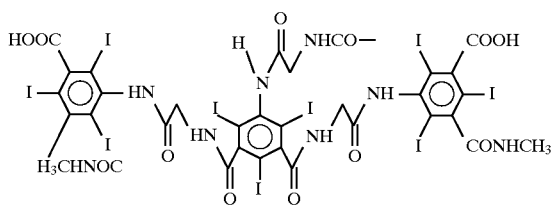

In a further aspect, the invention relates also to a process for preparing the polyiodinated compounds as defined above, characterized in that they are obtained, either:

1.i) by activation of a compound of formula A'(OH)$_m$, A' representing A as defined above and having m groups Y representing —CO, m being as defined above, the OH groups of A' being optionally protected by a protective group, with a chlorinating reagent to obtain a polyacid chloride of the formula:

A'—(Cl)$_{m'}$ followed by a ii) coupling of the compound of formula:

A'—(Cl⁻)$_m$ with m compounds of formula X'H, X' representing a group X as defined above in which Q, A₁, B₂, B₃ contains at least one group —NH—, —NR₅—, R₅ being as defined above, the OH groups of X' being optionally protected by a protective group, to obtain a compound of formula:

A'—(X')$_m$ iii) and deprotection of the protected hydroxyl groups of A' and X' so as to obtain a compound of formula A—(X)$_{m'}$ or 2.i) by direct activation of a compound of formula A'(OH)$_m$, as defined above, ii) coupling of the above compound with m compounds of formula X'H, X' being as defined above, so as to obtain a compound of formula:

A'—(X')$_m$ as defined above; and iii) deprotection of the protected OH groups of A' and X' to obtain a compound of formula:

A—(X)$_{m'}$ or 3.i) by reaction of a compound of formula A'(H)$_m$ in which A' represents a group A as defined above containing m groups Y representing —NH or —NR₅ and m being as defined above, the OH groups of A' being optionally protected by a protective group, with m acid chlorides of formula X'—(Cl)$_{m'}$, X' representing a group X as defined above containing at least one —CO group, the OH groups of which are optionally protected, so as to obtain a compound A'—(—X')$_{m'}$ deprotection of the OH groups of A' and X' so as to obtain a compound of formula A—(X)$_m$;

ii) reaction of a compound of formula A'—(H)$_m$, in which A' represents a group A as defined above containing a group Y representing —O— or >NCOR₅, the —OH groups of A' being optionally protected by a protective group, with m compounds of formula X'—L, X' representing a group X as defined above, the OH groups of which are protected, and L represents a leaving group, so as to obtain a compound of formula A'—(X')$_m$ as defined above, deprotection of the OH groups A' and X' so as to obtain the compound of formula:

A—(X)$_{m'}$

The reaction of step 1.i) takes place with a chlorinating reagent such as SOCl₂ PCl₅ or (CO)₂Cl₂ in a solvent such as DMAC, DMF, ethyl acetate or dichloromethane.

The reaction of step 1.ii) preferably takes place in a solvent such as DMF, DMAC or dichloromethane.

The reaction of step 2.i) takes place in the presence of a coupling reagent, in particular 1-ethoxycarbonyl-2-ethoxy-1,2-dihydroquinoline, 1-(3-dimethylaminopropyl)-3-ethylcarbodiimide or 1,3-dicyclohexylcarbodiimide, in a solvent such as DMAC, DMF, dichloromethane or water, optionally in the presence of a catalyst such as 1-hydroxy-1H-benzotriazole.

The reaction of step 3.i) is preferably carried out in a solvent such as DMF, DMAC, CH₂Cl₂ or dioxane.

The acid chlorides of step 3.ii) of formula X"CO—Cl are obtained, for example, from the corresponding compounds of formula X"COOH with a reagent such as SOCl₂, PCl₅ or (CO)₂Cl₂ in an organic solvent such as DMAC, DMF or CH₂Cl₂.

The leaving group L of step 3.ii) is preferably chosen from O-tosyl and O-mesyl groups and a halogen atom (Cl, Br, I).

The starting materials of formula A'(H)$_m$ or A"(COOH)$_m$ are obtained as described in the publications cited above with reference to the corresponding group A, or obtained from products sold on the market (for example α-, β- and γ-cyclodextrins marketed by Sigma, France) or prepared as described below.

The binding of the groups Q to the groups B₁, B₂ and B₃ is carried out in a manner known per se by acylation, amidation or alkylation reactions of the groups B in solvents such as DMF, DMAC or $CH_2Cl_2$, optionally in the presence of a base, in particular for the alkylation reactions.

The triiodinated starting materials corresponding to the groups $B_1$, $B_2$ and $B_3$ are obtained, in particular, according to the methods described in FR-A-2,272,640, FR-A-2,632,304, FR-A-2,673,180 and FR-A-2,656,865, or in the work "Radio Contrast Agents" (Sovak H. Ed. Sovak, Berlin, New York, Springer 1984).

When X represents a group D as described above, the compounds of generic formula I may be obtained from a compound of generic formula VI:

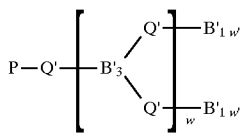
VI in which Q', $B'_1$ and $B'_3$ represent, respectively, the groups Q, $B_1$ and $B_3$, the OH groups of which are optionally protected, w and w' are as defined above and P is either a hydrogen atom, or a standard protective group for the amino or carboxyl group, or a leaving group (for example Cl, Br, I, OTs, OMs), which is coupled, after deprotection by removal of the group P, with the core of the molecule A by acylation or alkylation (reductive amination) reactions well known to a person skilled in the art, and the optionally protected OH functions are then deprotected to obtain the desired compound of generic formula I.

For example, coupling of the compounds of generic formula II is carried out with a compound of formula $A'(OH)_m$, for example trimesic acid, after activation of the carboxyl groups, for example using a carbodiimide, followed by a possible acylation of the free amine functions of the compound of general formula VI.

The compound of general formula VI may be prepared from the intermediate compounds of the following formulae VII and VIII:

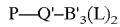 VII

 VIII in which P represents H, or a protective group for primary or secondary amine functions which is well known to a person skilled in the art, such as a phthalimido group, or a protective group for the carboxyl function, and Q', $B'_1$ and $B'_3$ represent, respectively, the groups Q, $B_1$ and $B_3$ in which the hydroxyl functions present are optionally protected, and L represents a leaving group (for example Cl, Br, I, OTs or OMs).

Thus, for n=0, the compound of formula VIII is deprotected by removal of the protective group P (for example by hydrazinolysis of the phthalimido groups), and the compound thus deprotected (for example the amine) obtained is reacted with a compound of formula VII (for example a diacid chloride) in standard solvents (DMAC, DMF, U-methylpyrrolidone, etc) in the presence of an organic or inorganic base to obtain a compound of formula

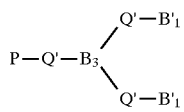

For n=1, after removal of the protective group P (for example by hydrazinolysis of the phthalimido groups), the compound obtained above is reacted with a compound of formula VII under the same conditions to obtain a compound of formula IX

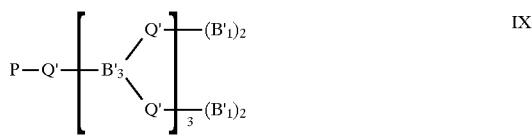
IX

For n=2, 3, 4, the compound obtained at the end of each step, the protective group of which has been removed, is reacted in the same manner with a compound of formula VII to obtain a compound of generic formula VI.

The subject of the invention is also the intermediate compounds of formula VI as defined above.

The subject of the invention is also contrast media which comprise at least one compound of formula I.

These contrast media are used in man and animals for radiological purposes.

The preferred pharmaceutical dosage form of the contrast media according to the invention consists of aqueous solutions or of suspensions of the compounds, preferably in double-distilled water. It can also take the form of a powder.

The aqueous solutions of the compounds of formula I can also contain certain additives, such as:
sodium chloride at concentrations between 0.1 and 10 mM,
disodium EDTA at concentrations of between 0.1 and 2 mM,
sodium citrate at concentrations of between 0.1 and 10 mM,
tris(hydroxymethyl)aminomethane hydrochloride,
tris(hydroxymethyl)aminomethane amine,
heparin at concentrations of between 10 and 100 units per 100 ml of solution,
sodium calcium edetate.

For use in X-ray radiography, the contrast medium according to the invention is administered at a useful dose varying from approximately 1 to 1000 ml of aqueous solution, in order to obtain concentrations varying from approximately 0.01 g of iodine/kg body weight to approximately 5 g of iodine/kg body weight, and preferably from approximately 0.1 g of iodine/kg body weight to 2 g of iodine/kg body weight.

These compositions may be administered via all the routes traditionally used for iodinated contrast media. Thus, when they occur in solution, they may be administered enterally or parenterally (oral, rectal, intravenous, intra-arterial, intra-articular or subarachnoid route, as well as via the bronchial, lymphatic and intra-uterine routes); preferably, the compounds are administered intravascularly.

When they take the form of a suspension in water or the form of a powder in a physiologically acceptable pharmaceutical formulation, the compositions according to the invention are preferably administered enterally, orally, rectally or bronchially.

The compositions of the invention can, in addition, take the form of liposomes, the compounds of formula I being encapsulated inside these liposomes.

In the case of an injection, the latter may be carried out by bolus or in perfusion.

An example of composition according to the present invention will be given below.

| Composition A | |
|---|---|
| Compound of Example 1 | 35.77 g |
| Water for injections Q.S. | 100 ml. |
| Composition B | |
| Compound of Example 1 | 53.65 g |
| Water for injections Q.S. | 100 ml. |

The subject of the invention is also a method of X-ray diagnosis, in particular of a subject's vascular compartment, characterized in that it comprises the intravenous or intra-arterial administration of a contrast medium as defined above, in a sufficient amount to render the said subject's vascular compartment opaque to X-rays, and the exposure of the said subject to a defined dose of X-rays, the injected dose varying from approximately 0.1 g of iodine/kg body weight to approximately 5 g of iodine/kg body weight, and preferably from approximately 0.1 g of iodine/kg body weight to approximately 2 g of iodine/kg body weight.

The preparation of intermediates compounds, as well as a few examples of compounds according to the invention, will be described below. Preparation of the compound $AH_3$ of formula:

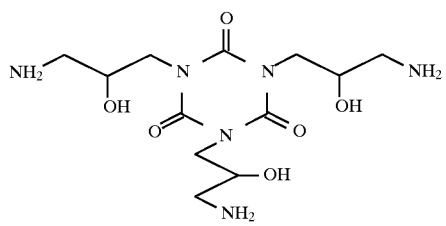

1) Preparation of N,N',N"-tris(2,3-epoxypropyl)-1,3,5-triazine-2,4,6(1H,3H,5H)-trione

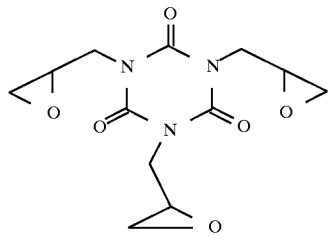

74 g (0.43 mol) of 70% meta-chloroperbenzoic acid suspended in 400 ml of dichloromethane are added to a mixture of 10 g (0.04 mol) of N,N',N"-triallyl-1,3,5-triazine-2,4,6(1H,3H,5H)-trione (commercially available from Aldrich—Strasbourg—France) and 100 ml of dichloromethane. Stirring is maintained for 6 days at room temperature.

After cooling and returning to room temperature, the solution is filtered; the peroxides contained in the filtrate are neutralized with 35 ml of 10% sodium sulphite solution. The organic phase is separated after settling has taken place and washed with twice 100 ml of 5% sodium bicarbonate solution. After settling has taken place, the organic phase is separated, dried over magnesium sulphate and evaporated.

10 g of white powder are obtained, equivalent to an 84% yield.

2) Preparation of N,N',N"-tris(2-hydroxyethyl-iminodibenzyl)-1,3,5-triazine-2,4,6(1H,3H,5H)-trione

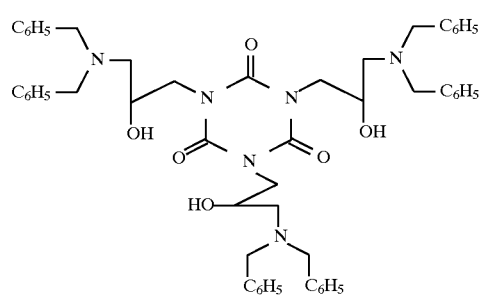

4.97 g (0.025 mol) of dibenzylamine are added to a solution of 2.5 g (0.008 mol) of N,N',N"-tris(2,3-epoxypropyl)-1,3,5-triazine-2,4,6(1N,3H,5H)-trione in 10 ml of dichloromethane. Stirring is maintained for two days at room temperature. The reaction medium is evaporated, and the product obtained is purified by chromatography with ethyl acetate. After evaporation of the organic phase, 3.6 g of beige powder are obtained, equivalent to a 50% yield.

3) Preparation of N,N'N"-tris(2-amino-3-hydroxypropyl)-1,3,5-triazine-2,4,6(1H,3H,5H)-trione

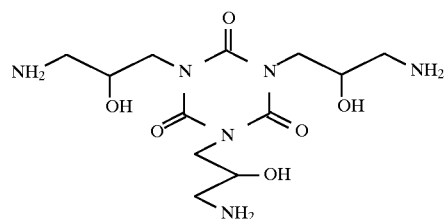

2 g of (0.002 mol) of N,N',N"-tris(2-hydroxyethyliminodibenzyl)-1,3,5-triazine-2,4,6(1H,3H,5H)-trione dissolved in 200 ml of methanol are hydrogenated at 8 bars and at 50° C. in the presence of hydrated palladium or charcoal (palladium content 50%) for 3 hours.

After filtration and evaporation, 500 mg of a white powder are obtained, equivalent to a 70% yield.

$^{13}C$ NMR (DMSO-$d_6$, 66.6 MHz)

43.8 ppm CH—$\underline{CH_2}$—NH$_2$
          |
          OH 45.9 ppm N—$\underline{CH_2}$—CH
                    |
                    OH 66.7 ppm CH$_2$—$\underline{CH}$—CH$_2$
                  |
                  OH 149.4 ppm $\underset{\underset{O}{\|}}{C}$ Preparation of the compound $A(OH)_3$ of formula:

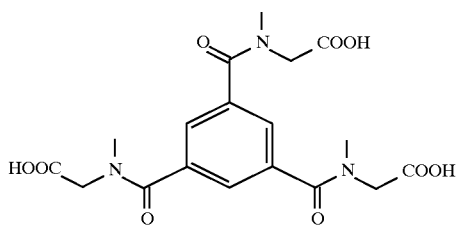

1) Esterification of sarcosine

The esterification of sarcosine is carried out according to the method described in Agric. Biol. Chem., 50 (3) 615, 1986.

2) Chlorination of the trimesic acid 73 g (0.35 mol) of trimesic acid (commercially available from the company SIGMA, France) are suspended in 300 ml of thionyl chloride. After reflux for 24 h, removal of the thionyl chloride and vacuum distillation, the acid trichloride is obtained in the form of a white solid.

(88.1 g, Yield: 95.5%, M.p.: 35° C.)

2.62 g (0.019 mol) of sarcosine ester in hydrochloride form, obtained above, 6.55 ml (0.047 mol) of triethylamine and then 1 g (0.0038 mol) of trimesic acid trichloride are added slowly to dichloromethane. After 6 h of reflux, cooling and filtration, 1.55 g of product in the form of a triester are obtained, equivalent to an 89% yield.

Rf ($CH_2Cl_2$/MeOH 9:1): 0.47

$^1$H NMR DMSO-$d_6$ 200 MHz 2.99 (s, 9H, NH—$\underline{CH}_3$); 3.68 (s, 9H, $CO_2\underline{CH}_3$); 4.16 (s, 6H, $CH_2$); 7.43 (s, 3H, CH).

3) Saponification of the triester 0.61 g (0.0013 mol) of the triester prepared in the preceding step is dissolved in 8 ml of methanol. 0.52 g (0.013 mol) of sodium hydroxide dissolved in 2 ml of water is added. After 12 h at room temperature, acidification, filtration and evaporation, 0.55 g of triacid is obtained.

$^1$H NMR DMSO-$d_6$ 200 MHz 2.95 (s, 9H, CH—$\underline{CH}_3$); 4.1 (s, 6H, $CH_2$); 7.4 (s, 3H, CH); 7.77 (s, 3H, COOH).

Preparation of the compound $AH_4$ of formula:

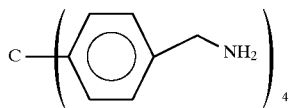

The preparation is carried out from the compound:

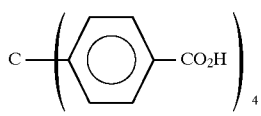

prepared according to the method described in Angew. Chem. Int. Ed. Engl. 25, 1986, 1097.

The conversion -phenyl-$CO_2H \rightarrow$ phenyl-$NH_2$ is carried out according to the method described in JACS, 101, p. 2728, 1979.

EXAMPLE 1

Preparation of the compound of formula:

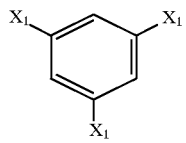

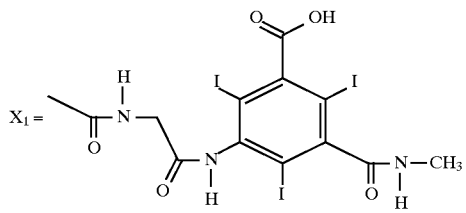

4 g (0.019 mol) of trimesic acid, 37.11 g (0.059 mol) of 3-(N-methylcarbamoyl)-5-aminoacetamido-2,4,6-triiodobenzoic acid prepared according to the method described in U.S. Pat. No. 4,014,986, 10.49 g (0.0685 mol) of hydroxybenzotriazole, 10 ml of triethylamine and 13.14 g (0.0685 mol) of 1-(3-dimethylaminopropyl)-3-ethylcarboduimide hydrochloride (EDCI) are dissolved in 1 of DMF. After stirring at room temperature for 12 h followed by evaporation of the solvent, the residue is triturated in $CH_2Cl_2$. The solid obtained is purified by dissolution in aqueous ammonia and then precipitated in an acid medium.

32.7 g of product in the form of white powder are obtained, equivalent to an 84% yield.

TLC $SiO_2$ (AcOEt/isopropanol/$NH_3$, 35:35:40)

Rf: 0.16

$^1$H NMR DMSO-$d_6$ 200 MHz 2.7 (s, 9H, $CH_3$); 3.3 (m, 3H, $CO_2H$); 4.2 (s, 6H, $CH_2$); 8.45 (dq, 3H, CO—$\underline{NH}$—$CH_3$); 8.6 (s, 3H, CH); 9.05 (t, 3H, CO—$\underline{NH}$—$CH_2$); 10.15 (d, 3H, $C_{ar}$—$\underline{NH}$—CO)

$^{13}$C NMR DMSO-$d_6$ 66.6 MHz 26 (3$CH_3$); 43 (3$CH_2$); 88.8, 97.5, 99.2 (9$C_{ar}$—I); 129 (3$C_{ar}$—H); 134.4 (3$C_{ar}$—CO); 143, 149, 150.5 (9$C_{ar}$—I); 165.6, 167.5, 169.7 (12CO).

EXAMPLE 2

Preparation of the compound of formula:

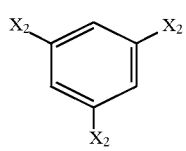

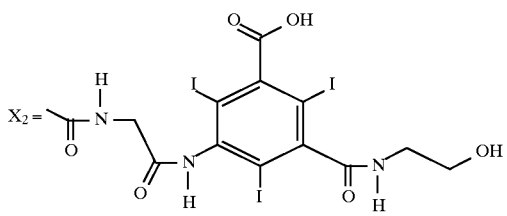

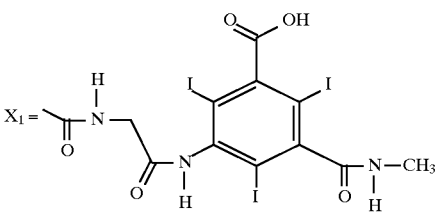

3 g (0.014 mol) of trimesic acid, 29.16 g (0.044 mol) of 3-[N-(hydroxyethyl)carbamoyl]-5-aminoacetamido-2,4,6-triiodobenzoic acid prepared according to the method described in U.S. Pat. No. 4,014,986, 7.65 g (0.05 mol) of hydroxybenzotriazole, 10 ml of triethylamine and 9.58 g (0.05 mol) of EDCI are dissolved in 0.8 l of DMF. After stirring of the mixture at room temperature for 12 h followed by evaporation of the solvent, the residue is triturated in $CH_2Cl_2$. The solid obtained is purified by dissolution in aqueous ammonia and is then precipitated in an acid medium.

28 g of the product in the form of a white powder are obtained, equivalent to a 90% yield.

TLC $SiO_2$ (AcOEt/isopropanol/$NH_3$, 35:35:40)

Rf: 0.15

$^1$H NMR DMSO-$d_6$ 200 MHz 3.2 (m, 6H, $CH_2$—$\underline{CH_2}$—OH); 3.5 (m, 6H, $\underline{CH_2}$—$CH_2$OH); 4.2 (s, 6H, CONH—$\underline{CH_2}$—CONH); 8.6 (m, 3H, CO$\underline{NH}$—$CH_2CH_2$OH); 8.6 (s, 3H, CH); 9.06 (t, 3H, CO—$\underline{NH}$—$CH_2$CO); 10.2 (d, 3H, $C_{ar}$—$N\underline{H}$—CO).

$^{13}$C NMR 66.6 MHz DMSO-$d_6$ 40.3 (3$\underline{CH_2}CH_2$OH); 41.7 (3CONH$\underline{CH_2}$CONH); 59.2 (3$\underline{CH_2}$OH); 86.8, 97.5, 99.3 (9$C_{ar}$—I); 129.5 (3$C_{ar}$—H); 134.4 (3$C_{ar}$—CO); 142.8, 149, 150.2 (9$C_{ar}$iodinated); 165.6, 167.3, 167.5, 169.3, 169.7 (12 CO).

EXAMPLE 3

Preparation of the compound of formula:

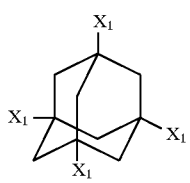

0.92 g (0.0048 mol) of EDCI is added to a solution of 0.31 g (0.001 mol) of 1,3,5,7-tetracarboxyadamantane prepared according to the method described in J. Org. Chem. (1992), 57, 358, 2.5 g (0.004 mol) of 3-(N-methylcarbamoyl)-5-aminoacetamido-2,4,6-triiodobenzoic acid, 0.74 g (0.0048 mol) of hydroxybenzotriazole and 1.4 ml (0.01 mol) of triethylamine in 50 ml of dimethylformamide. The mixture is stirred for 12 hours at room temperature and then evaporated to dryness. The residue is taken up in 100 ml of $CH_2Cl_2$ with stirring and is then filtered off. The solid obtained is dissolved in 20 ml of water in a sufficient amount of sodium hydrogen carbonate solution, and the solution is reprecipitated at pH 2. After filtration and drying, 2.5 g of a white powder are obtained, equivalent to a 92% yield.

TLC ($SiO_2$) Isopropanol/AcOEt/$NH_3$, 35:35:40

Rf: 0.15

$^1$H NMR DMSO-$d_6$ 200 MHz 1.9 (s, 12H, adamantane $CH_2$); 2.7 (s, 12H, $CH_3$); 3.0 (m, 4H, $CO_2H$); 3.9 (s, 8H, $CH_2$); 7.5 (dq, 4H, CO$\underline{NH}$, $CH_3$); 8.5 (d, 4H, CO—$\underline{NH}$—$CH_2$); 9.95 (d, 4H, $C_{ar}$—$\underline{NH}$—CO).

$^{13}$C NMR DMSO-$d_6$ 66.6 MHz 27 ($CH_3$); 38 (adamantane C); 42.5 (adamantane $CH_2$); 43 ($CH_2$); 88.5, 97.5, 100.0 (C—I); 143, 149, 153 $C_{ar}$); 168, 170, 177 (CO).

EXAMPLE 4

Preparation of the compound of formula:

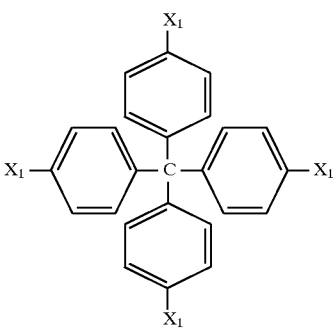

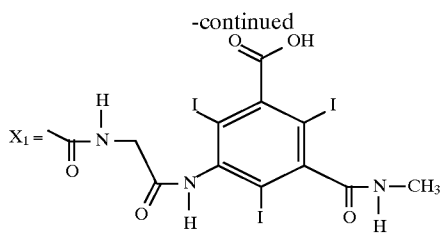

500 mg (0.001 mol) of 4,4',4",4'"-tetracarboxytetraphenylmethane prepared according to the method described in Angew. Chem. Int. Ed. Engl., 25 (1986) no. 12, 1097–1098 and J.A.C.S. (1990) 112, 1546–1554, 2.76 g (0.0044 mol) of 3-(N-methylcarbamoyl)-5-aminoacetamido-2,4,6-triiodobenzoic acid, 0.674 g (0.005 mol) of hydroxybenzotriazole and 0.7 ml (0.005 mol) of triethylamine are dissolved in 100 ml of DMF. 0.843 g (0.005 mol) of EDCI are introduced into the reaction mixture. After stirring for 24 h at room temperature, the solvent is removed under vacuum and the residue is crystallized in $CH_2Cl_2$. The solid is solubilized in aqueous ammonia and precipitated in an acid medium.

2.5 g of the product are obtained, equivalent to an 85% yield.

TLC ($SiO_2$) AcOEt/isopropanol/$NH_4OH$, 35:35:40

Rf: 0.12

$^1H$ NMR DMSO-$d_6$ 200 MHz 2.7 (s, 12H, $CH_3$); 3.3 (m, 4H, $CO_2H$); 4.1 (s, 8H, $CH_2$); 7.25, 7.9 (dd, 16H, Φ—H); 8.4, 8.5 (dd, 4H, CO—NH—$CH_3$); 8.8 (m, 4H, CO—NH—$CH_2$); 10.05 (d, 4H, Φ—NH—CO).

EXAMPLE 5

Preparation of the compound of formula:

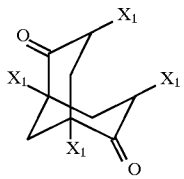

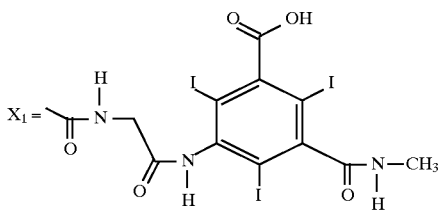

2 g (0.0052 mol) of tetramethyl-1,3,5,7-tetracarboxy-2,6-dioxobicyclo[1.3.3]nonane prepared according to the method described in J. Org. Chem. (1992) 57, 358 are stirred in 14 ml of 2N sodium hydroxide and 15 ml of methanol for 48 h at 50° C.

The solution is evaporated to dryness and the residue taken up in 10 ml of water. After the addition of 12N hydrochloric acid to pH 1, the mixture is left to crystallize for 16 h. After filtration and drying, 0.6 g of white powder are obtained, equivalent to a 35% yield.

TLC ($SiO_2$) MeOH/AcOEt, 5:5-Rf: 0.43

IR (KBr) 3000, 2960, 1680, 1440, 1400, 1280, 1240 $cm^{-1}$ $^{13}C$ NMR DMSO-$d_6$ 66.6 MHz 28.1, 35.7 ($CH_2$); 42.4 (CH); 54.8 (C); 172.1 (CO); 208.5 (C=O)

By adopting the procedure described in Example 3 above, the compound of the title is obtained.

EXAMPLE 6

Preparation of the compound of formula:

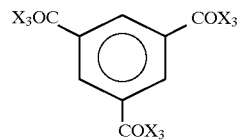

with

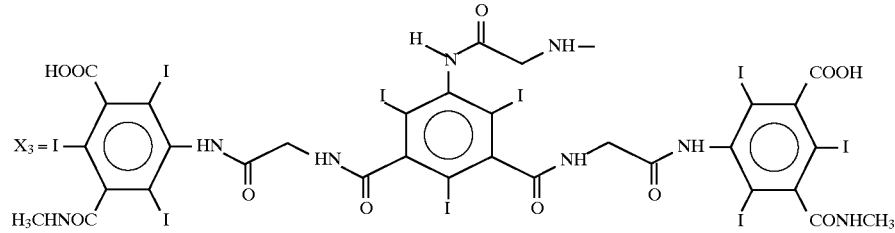

1) Preparation of the compound of formula:

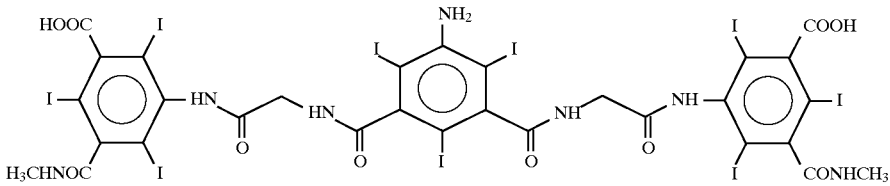

N,N'-bis{N-[2,4,6-triiodo-3-carboxy-5-(N-methylcarbamoyl)phenyl]carbamoylmethyl}-5-amino-2,4,6-triiodoisophthalamide 26.4 g (0.042 mol) of 2,4,6-triiodo-5-amino-N-methylisophthalamic acid are added rapidly to a solution of 10 g (0.0168 mol) of 5-amino-2,4,6-triiodoisophthaloyl chloride in 30 cm³ of dimethylacetamide with stirring. The mixture is then heated at 50° C. for 3 h and thereafter precipitated in HCl (10N). After stirring for 24 h, the precipitate is filtered off, washed with water and dichloromethane and then dried.

20 g (67%) of product are obtained.

TLC (SiO₂) toluene/methyl ethyl ketone/HCOOH, 60:25:20

Rf: 0.13

$^{13}$C NMR DMSO-d$_6$ 66.6 MHz 147 ppm (C—NH);
‖
O 143 ppm (COOH)
Iodinated aromatic C
100 ppm; 98 ppm; 90 ppm; 82 ppm;
CH₂ (on amine) 43 ppm;
CH₃

(on amide NH—C—)
‖
O 26 ppm.

2) Preparation of the compound of formula:

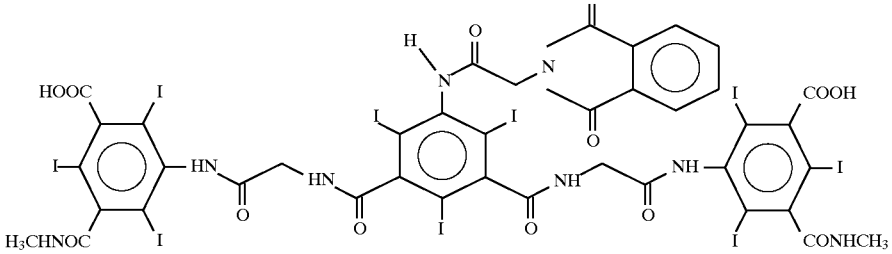

170 ppm

O
‖
C (amide group on aromatic ring)

C
‖
O (carboxyl group on aromatic ring)

Aromatic C 151 ppm (NH₂); 150 ppm (NH—C=O); 149 ppm (C—NH)
‖
O

N,N'-bis{N-[2,4,6-triiodo-3-carboxy-5-(N-methylcarbamoyl)phenyllcarbamoylmethyl}-5-[N-(phthalimidoacetyl)amino]-2,4,6-triiodoisophthalamide 1.2 g (5.37×10⁻³ mol) of phthaloylglycyl chloride are added to a solution of 1 g (5.48×10⁻⁴ mol) of the product obtained in the preceding step in 2 cm³ of dimethylacetamide with stirring. The reaction medium is stirred for 24 h at room temperature and is then precipitated in hot water. The precipitate is filtered off, washed with hot water and then dichloromethane and dried.

TLC (SiO₂) ethyl acetate/isopropanol/NH₃, 35:35:40. Rf: 0.27

The product obtained is deprotected in a traditional manner by treatment with hydrazine. After coupling to trimesic acid according to the method described in Example 1 above, the product of the title is obtained.

EXAMPLE 7

Preparation of the compound of formula:

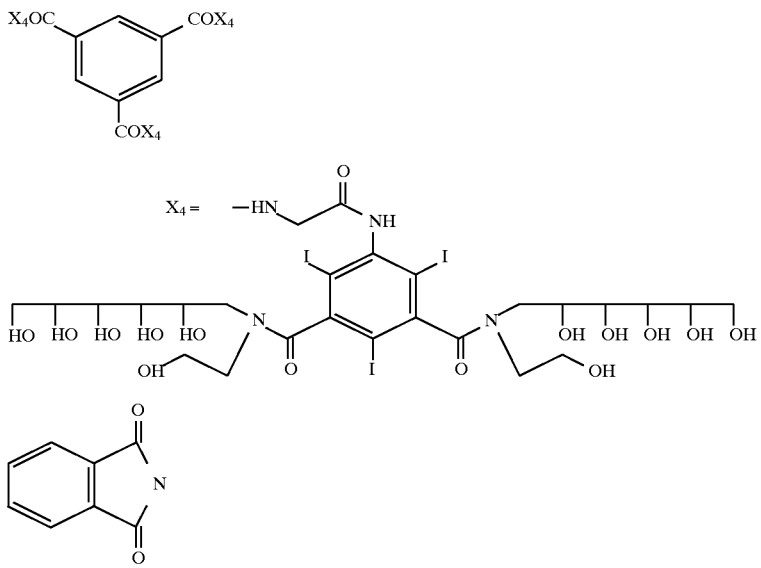

1) Preparation of the compound of formula:

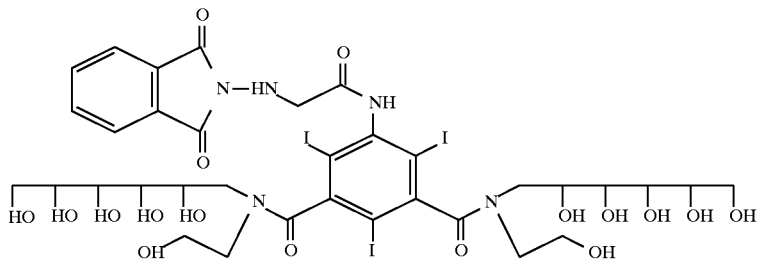

300 g (0.38 mol) of 5-[N-(phthalimidoacetyl)amino]-2,4,6-triiodoisophthaloyl chloride are added to a solution of 258.9 g (1.149 mol) of 1-deoxy-1-(2-hydroxyethylamino)-D-glucitol and tributylamine (273.9 ml; 1.149 mol) in 2 liters of dimethylacetamide. The mixture is stirred overnight at room temperature. After evaporation of the solvent and precipitation in dichloromethane, the product is dissolved in water and purified by passing it through an ion exchange resin (Amberlite IRN 77). After evaporation, 350 g (80% Yld.) of product are obtained.

$^{13}$C NMR DMSO-$d_6$ 66.6 MHz
170, 167, 166, 165 ppm (C=O)
149, 143 ppm (aromatic C)
135, 132, 123 ppm (phthalimido aromatic C)
99, 91 ppm (iodinated aromatic C)
73, 71, 69 ppm (amine alcohol CH)
63, 59, 58.5, 57 ppm (amine alcohol CH$_2$)
52.5, 52, 49, 48.5 ppm (CH$_2$ α to N of the amine alcohol)
41 ppm (CH$_2$ α to the phthalimido).

2) Preparation of the compound of formula: HX$_4$ 275 g (0.22 mol) of the compound of Example 7.1 are dissolved in 1.4 liters of water in the presence of 33.2 ml (0.66 mol) of hydrazine hydrate. The mixture is heated to 80° C. for 2 hours and then, after returning to room temperature, acidified with 53 ml of hydrochloric acid (10N). The insoluble matter is filtered off and the solution is purified by passage through ion exchange resins (Amberlite IRA 67 and IRC 50). After evaporation, 188.7 g of product are obtained (Yld.=97%).

$^{13}$C NMR DMSO-$d_6$ 66.6 MHz
173, 171, 170 ppm (C=O)
149, 143 ppm (aromatic C)
99, 91 ppm (iodinated aromatic C)
73, 71, 69 ppm (amine alcohol CH)
63, 59, 58.5, 57 ppm (amine alcohol CH$_2$)
52.5, 52, 49, 48.5 ppm (CH$_2$ α to amine alcohol N)
45 ppm (CO—$\underline{CH_2}$—NH$_2$).

3) Preparation of the compound of the title 15 g (0.0146 mol) of the compound of Example 7.2 are dissolved in 320 ml of dimethylformamide in the presence of 0.927 g (4.4×10$^{-3}$ mol) of trimesic acid, 2,15 g (0.016 mol) of 1-hydroxybenzotriazole, 2.34 mol (0.0168 mol) of triethylamine and 3.05 g (0.0159 mol) of EDCI. After stirring for 24 hours at room temperature, the solvent is removed under vacuum and the residue is triturated in CH$_2$Cl$_2$. After purification on silanized silica (SiRP2, elution with water), 8.3 g of the expected product are obtained (Yld.=58%).

$^{13}$C NMR DMSO-$d_6$ 66.6 MHz:
170, 167, 165.5 ppm (C=O)
149, 143 ppm (aromatic C)
134, 129.5 ppm (trimesic aromatic C)
99, 91 ppm (iodinated aromatic C)
10 73, 71, 69 ppm (amine alcohol CH)
63, 59, 58.5, 57 ppm (amine alcohol CH$_2$)
52.5, 52, 49, 48.5 ppm (CH$_2$ α to amine alcohol N)
43 ppm (CO—NH—$\underline{CH_2}$-CONH).

EXAMPLE 8

Preparation of the compound of formula:

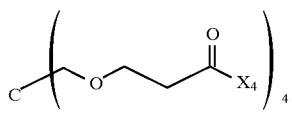

with $X_4$ as defined in Example 7

From the tetraacid obtained according to the method described in G. R. Newkome, C. N. Moorefield and G. R. Baker; Aldrichimica Acta, Vol. 25, No. 2, 1992, p. 31 and of the compound of Example 7.2, the compound of the title is prepared according to the coupling method described in Example 7.

EXAMPLE 9

Preparation of the compound of formula:

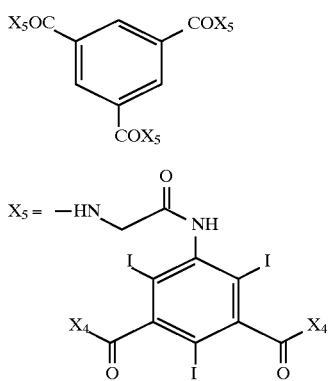

with $X_4$ as defined in Example 7.

1) Preparation of the compound of formula:

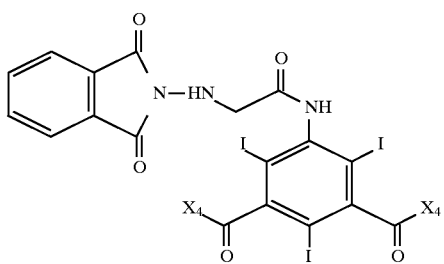

150 g (0.146 mol) of the compound of Example 7.2 are added to a solution of 400 ml of dimethylacetamide containing 35 ml of tributylamine and 47.5 g (0.06 mol) of 5-[N-(phthalimidoacetyl)amino]-2,4,6-triiodoisophthaloyl chloride. The reaction medium is heated to 50° .C for 2 hours and then concentrated to dryness. The product is then triturated in methylene chloride and thereafter purified by chromatography on silanized silica (SiRP2, elution with water). 110 g (Yld.=80%) of the expected product are thereby obtained.

$^{13}$C NMR DMSO-$d_6$ 66.6 MHz
170, 167, 166, 165 ppm (C=O)
149, 148.5, 143.5, 143 ppm (aromatic C)
135, 132, 123 ppm (phthalimido aromatic C)
99.5, 99, 91, 90.5 ppm (iodinated aromatic C)
73, 71, 69 ppm (amine alcohol CH)
63, 59, 58.5, 57 ppm (amine alcohol CH$_2$)
52.5, 52, 49, 48.5 ppm (CH$_2$ α to amine alcohol N)
44 ppm (CO—NH—CH$_2$—CONH)
41 ppm (CH$_2$ α to phthalimido)

2) Preparation of the compound of formula: $X_5$H 110 g (0.04 mol) of the compound of Example 9.1 are dissolved in 370 ml of water in the presence of 6 ml (0.12 mol) of hydrazine hydrate. The mixture is heated to 80° C. for 2 hours and then, after returning to room temperature, acidified with 16 ml of hydrochloric acid (10N). The insoluble matter is filtered off and the solution is purified by passage through ion exchange resins (Amberlite IRA67 and IRL50). After evaporation, 99 g of product are obtained (Yld.-94%).

$^{13}$C NMR DMSO-$d_6$ 66.6 MHz
170, 168, 165 ppm (C=O)
149, 148.5, 143.5, 143 ppm (aromatic C)
99.5, 99, 91, 90.5 ppm (iodinated aromatic C)
73, 71, 69 ppm (amine alcohol CH)
63, 59, 58.5, 57 ppm (amine alcohol CH$_2$)
52.5, 52, 49, 48.5 ppm (CH$_2$ α to amine alcohol N)
45 ppm (NH—CO—CH$_2$—NH$_2$)
43 ppm (CONH—CH$_2$—CONH).

3) Preparation of the compound of the title

By reaction between the compound of Example 9.2 and trimesic acid under the usual coupling conditions described in Example 7, the compound of the title is obtained in an 80% yield.

$^{13}$C NMR DMSO-$d_6$ 66.6 MHz
170, 167, 166, 165 ppm (C=O)
149, 148.5, 143.5, 143 ppm (aromatic C)
135, 127 ppm (trimesic aromatic C)
100, 99.5, 90.5, 90 ppm (iodinated aromatic C)
73, 71, 69 ppm (amine alcohol CH)
63, 59, 58.5, 57 ppm (amine alcohol CH$_2$)
52.5, 52, 49, 48.5 ppm (CH$_2$ α to amine alcohol N)
43 ppm (CONH—CH$_2$—CONH).

EXAMPLE 10

Preparation of the compound of formula:

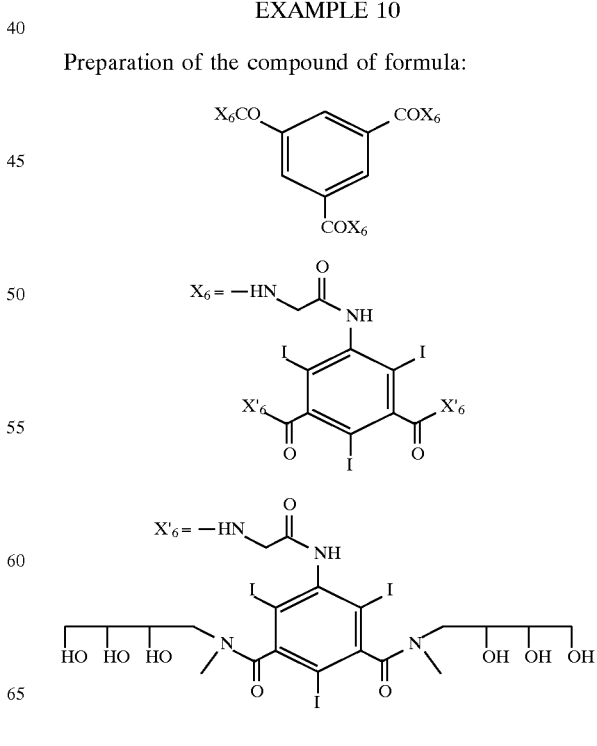

1) Preparation of the compound of formula:

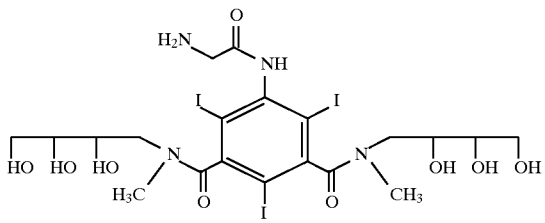

150 g (0.19 mol) of 5-[N-(phthalimidoacetyl)amino]-triiodoisophthaloyl chloride are reacted with 78 g (0.578 mol) of N-methylaminobutanetriol according to the procedure described in Example 7.1. 186.2 g (Yld.=99%) of the diamidation product are thereby obtained, which product is subjected to hydrazinolysis under the conditions of Example 7.2 to obtain the expected product in a 74% yield.

$^{13}$C NMR DMSO-$d_6$ 66.6 MHz
171, 170, 165 ppm (C=O)
150, 144 ppm (aromatic C)
99, 90 ppm (iodinated aromatic C)
72, 66 ppm (amine alcohol CH)
63 ppm (amine alcohol CH$_2$)
55, 51 ppm (CH$_2$ α to amine alcohol N)
45 ppm (NH—CO—CH$_2$—NH$_2$)
37, 34 ppm (CH$_3$—N).

2) Preparation of the compound of formula: X$_6$H 80 g (0.094 mol) of the compound of Example 10.1 are reacted with 30.7 g (0.039 mol) of 5-[N-(phthalimidoacetyl)amino]-2,4,6-triiodoisophthalazoyl chloride according to the procedure of Example 9.1. 72.4 g (Yld.=77%) of the diamidation product are thereby obtained, which product is subjected to hydrazinolysis under the conditions of Example 9.2 to obtain the expected product in a 91% yield.

$^3$C NMR DMSO-$d_6$ 66.6 MHz
171, 170, 165 ppm (C=O)
150, 149.5, 144.5, 144 ppm (aromatic C)
100, 99.5, 90.5, 90 ppm (iodinated aromatic C)
72, 66 ppm (amine alcohol CH)
63 ppm (amine alcohol CH$_2$)
55, 51 ppm (CH$_2$ α to amine alcohol N)
45 ppm (NHCO—CH$_2$—NH$_2$)
44 ppm (CONH—CH$_2$—CONH)
37, 34 ppm (CH$_3$—N).

3) Preparation of the compound of the title

By reaction between the compound of Example 10.2 and trimesic acid under the usual coupling conditions described in Example 7, the compound of the title is obtained in a 90% yield.

$^{13}$C NMR DMSO-$d_6$ 66.6 MHz
170, 167, 166 165 ppm (C=O)
150, 149.5, 144.5, 144 ppm (aromatic C)
135, 127 ppm (trimesic aromatic C)
100, 99.5, 90.5, 90 ppm (iodinated aromatic C)
72, 66 ppm (amine alcohol CH)
63 ppm (amine alcohol CH$_2$)
55, 51 ppm (CH$_2$ α to amine alcohol N)
44 ppm (—CO—NH—CH$_2$—CONH)
37, 34 ppm (CH$_3$—N)

EXAMPLE 11

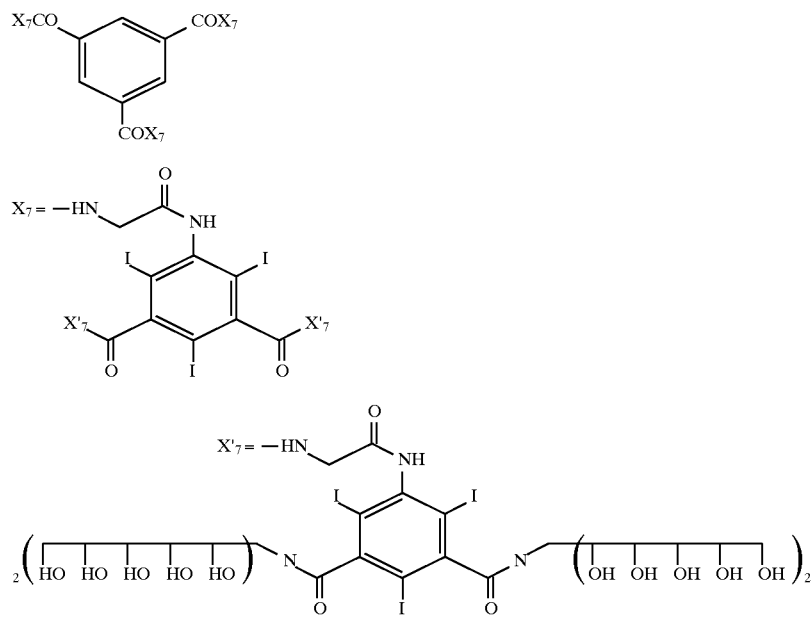

1) Preparation of the compound of formula: X$_7$H 208 g (0.24 mol) of 5-[N-(phthalimidoacetyl)amino]-2,4,6-triiodoisophthaloyl chloride are added to a solution of 416 g (1.2 mol) of bis(1-deoxy-D-sorbit-1-yl)-amine and 100 ml (0.72 mol) of triethylamine in 2 liters of 1-methyl-2-pyrrolidinone (NMP). The mixture is heated at 70° C. for 24 hours. The insoluble matter is then filtered off and the solvent is removed under vacuum. The product is then purified as in Example 7.1 and thereafter subjected to hydrazinolysis under the usual conditions (Example 7.2). It is then reacted with 0.42 equivalent of 5-[N-(phthalimidoacetyl)amino]-2,4,6-triiodoisophthaloyl chloride under the conditions of Example 9.1 and thereafter subjected to hydrazinolysis under the usual conditions (Example 9.2). The product is obtained in a 51% overall yield.

$^{13}$C NMR DMSO-d$_6$ 66.6 MHz
170, 167, 166, 165 ppm (C=O)
149, 148.5, 143, 142.5 ppm (aromatic C)
99, 98.5, 91, 90.5 ppm (iodinated aromatic C)
73, 71, 69 ppm (amine alcohol CH)
63 ppm (amine alcohol CH$_2$)
54.5, 54, 49.5, 49 ppm (CH$_2$ α to amine alcohol N)
44 ppm (NHCO—CH$_2$—NH$_2$)
43 ppm (CONH—CH$_2$—CONH).

2) Preparation of the compound of the title

By reaction between the compound of Example 11.1 and trimesic acid under the usual coupling conditions described in Example 7, the product of the title is obtained in an 80% yield.

$^{13}$C NMR DMSO-d$_6$ 66.6 MHz
170, 167, 166, 165 ppm (C=O)
149, 148.5, 143, 142.5 ppm (aromatic C)
135, 127 ppm (trimesic aromatic C)
99, 98.5, 91, 90.5 ppm (iodinated aromatic C)
73, 71, 69 ppm (amine alcohol CH)
63 ppm (amine alcohol CH$_2$)
54.5, 54, 49.5, 49 ppm (CH$_2$ α to amine alcohol N)
44 ppm (CONH—CH$_2$—CONH).

EXAMPLE 12

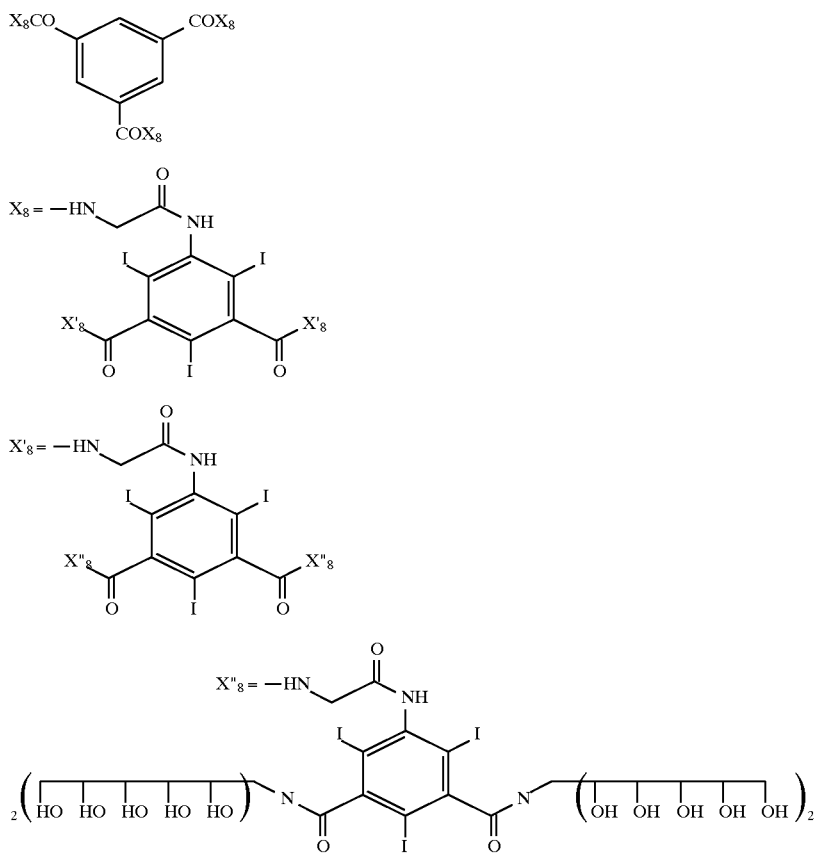

The product of Example 11.1 is reacted with 0.42 equivalent of 5-[N-(phthalimidoacetyl)amino]-2,4,6-triiodoisophthaloyl chloride under the conditions of Example 9.1, and then subjected to hydrazinolysis in the usual manner (Example 9.2). Then, by coupling trimesic acid under the usual conditions described in Example 7, the product of the title is obtained.

EXAMPLE 13

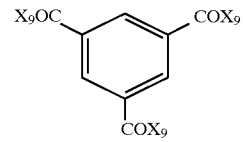

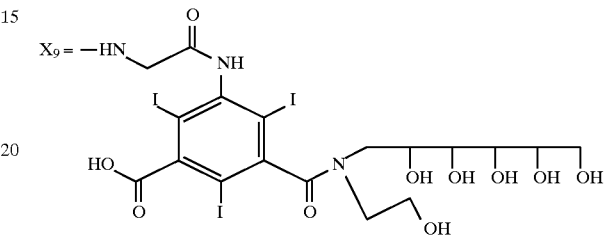

1) Preparation of the compound of formula:

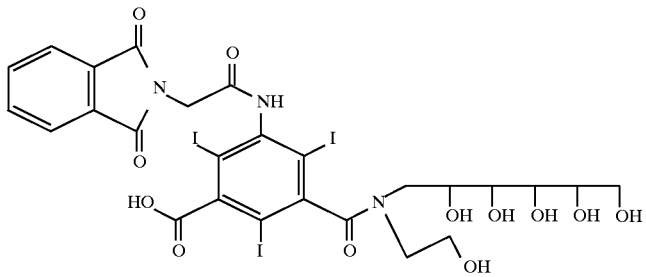

119.5 g (0.13 mol) of 5-(phthalimidoacetyl)amino]-2,4,6-triiodoisophthaloyl chloride are added to a solution of 41.53 g (0.14 mol) of 1-deoxy-1-(2-hydroxyethylamino)-D-glucitol and triethylamine (19.5 ml; 0.14 mol) in 700 ml of diethylacetamide. The mixture is stirred at room temperature for 24 hours. 300 ml of water are added, and stirring is maintained for 48 hours while heating at 45° C. The solvent is then evaporated off under vacuum and the product is purified on ion exchange resin (Amberlite IRN 77) and on silanized silica (SiRP2, elution with water). 26 g (Yld.=38%) of product are obtained.

$^{13}$C NMR DMSO-$d_6$ 66.6 MHz
170, 169.5, 167, 165 ppm (C=O)
150, 147, 142 ppm (aromatic C)
135, 132, 124 ppm (phthalimido C)
100, 98, 90 ppm (iodinated aromatic C)
73, 71, 69 ppm (amine alcohol CH)
63, 59, 58 ppm (amine alcohol CH$_2$)
52.5, 52, 49, 48.5 ppm (CH$_2$ α to amine alcohol N)
41 ppm (CH$_2$ α to phthalimido).

2) Preparation of the compound of formula: X$_9$H 25 g (0.026 mol) of the product of Example 13.1 are subjected to hydrazinolysis under the usual conditions described in Example 7.2 to obtain the expected product in a 55% yield.

$^{13}$C NMR DMSO-$d_6$ 66.6 MHz
172, 171, 170 ppm (C=O)
157, 147, 142 ppm (aromatic C)
100, 98, 90 ppm (iodinated aromatic C)
73, 71, 69 ppm (amine alcohol CH)
63, 59, 58 ppm (amine alcohol CH$_2$)
52.5, 52, 49, 48.5 ppm (CH$_2$ α to amine alcohol N)
43 ppm (NHCO—CH$_2$—NH$_2$).

3) Preparation of the compound of the title 11.5 g (0.014 mol) of the product of Example 13.2 are reacted with trimesic acid under the usual coupling conditions described in Example 7 to obtain the product of the title in a 51% yield.

$^{13}$C NMR DMSO-$d_6$ 66.6 MHz
170, 167, 165 ppm (C=O)
157, 147, 142 ppm (aromatic C)
134, 130 ppm (trimesic aromatic C)
100, 98, 90 ppm (iodinated aromatic C)
73, 71, 69 ppm (amine alcohol CH)
63, 59, 58 ppm (amine-alcohol CH$_2$)
52.5, 52, 49, 48.5 ppm (CH$_2$ α to amine alcohol N)
42 ppm (CONH—CH$_2$—CONH).

EXAMPLE 14

Preparation of the compound of the formula

The product of Example 13.2 is reacted with 0.42 equivalent of 5-[N-(phthalimidoacetyl)amino]-2,4,6-triiodoisophthaloyl chloride under the conditions of Example 9.1 and then subjected to hydrazinolysis in the usual manner (Example 9.2). Then, by coupling with trimesic acid under the conditions of Example 7, the product of the title is obtained in a 12% overall yield.

$^{13}$C NMR DMSO-$d_6$ 66.6 MHz
170, 167, 166, 165 ppm (C=O)
150, 149.5, 147, 146.5, 142, 142.5 ppm (aromatic C)
135, 128 ppm (trimesic aromatic C)
100, 99.5, 98, 97.5, 90.5, 90 ppm (iodinated aromatic C)
73, 71, 69 ppm (amine alcohol CH)
63, 59, 58 ppm (amine alcohol CH$_2$)
52.5, 52, 49, 48.5 ppm (CH$_2$ α to amine alcohol N)
44 ppm (CONH—CH$_2$—CONH).

EXAMPLE 15

Preparation of the compound:

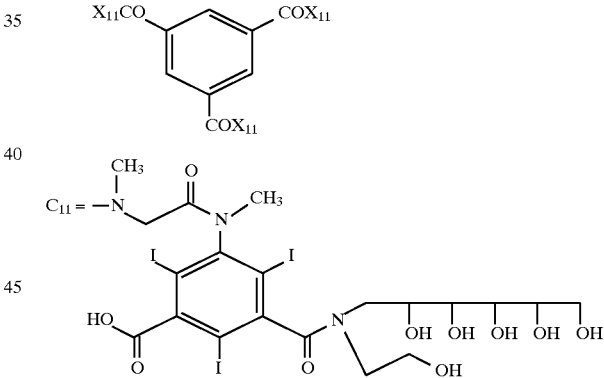

5-Amino-2,4,6-triiodoisophthalic acid is N-monomethylated (Yld.=62%) according to a procedure described in FR Patent no. 2,110,179. This product is then chlorinated, acylated with chloroacetyl chloride (Yld.=70%), diamidated in the presence of 1-deoxy-1-(2-hydroxyethylamino)-D-glucitol (Yld.=65%) and reacted with methylamine (Yld.=50%) under the conditions described in Patent WO 93/1007 of 27th May 1993. The product thereby obtained may be coupled with trimesic acid under the usual conditions (Example 7) to obtain the product of the title.

We claim:

1. Polyiodinated compounds with a single molecular weight having a molecular concentration of iodine of greater than 20% by weight, a molecular weight above 2,000 and below 50,000, and containing at least one group of formula

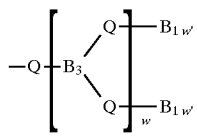

with $w = \Sigma_0^n 2^n$ and $w' = 2^n$, n representing an integer from 0 to 4, the groups Q, which may be identical to or different from one another, represent a single bond or a group selected from the group consisting of:

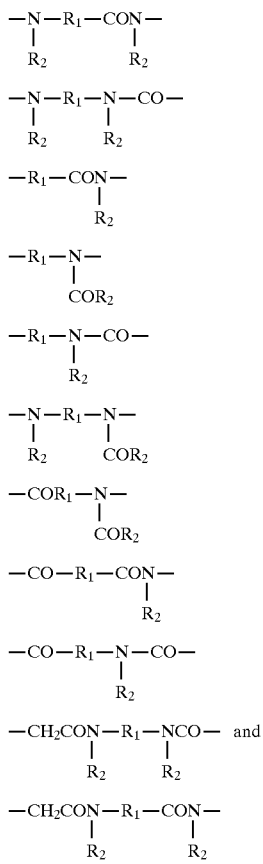

in which:

$R_1$ is selected from the group consisting of an alkylene group having a linear or branched $C_1$–$C_{10}$ chain, a hydroxy- or polyhydroxyalkylene group having a linear or branched $C_1$–$C_{10}$ chain, a ($C_1$–$C_5$ alkoxy)alkylene group having a linear or branched $C_1$–$C_{10}$ chain, a hydroxy- or polyhydroxy($C_1$–$C_{10}$ alkoxy)alkylene group having a linear or branched chain, and a single bond, and the $R_2$ groups identical or different being selected from H, the group consisting of an alkyl group having a linear or branched $C_1$–$C_{10}$ chain, a hydroxy- or polyhydroxyalkyl group having a linear or branched $C_1$–$C_{10}$ chain, a ($C_1$–$C_5$ alkoxy)alkyl group having a linear or branched $C_1$–$C_{10}$ chain and a hydroxy- or polyhydroxy($C_1$–$C_5$ alkoxy)alkyl group having a linear or branched chain;

the groups $B_1$, which may be identical to or different from one another, represent the residue of an aromatic group containing at least three iodine atoms, of formula:

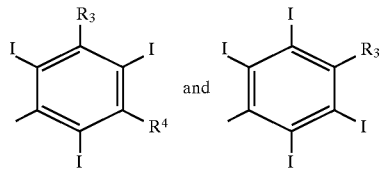

in which $R_3$ is selected from the group consisting of:
a group —COO⁻ M⁺ with M⁺ representing H⁺ or a physiologically acceptable cation of an organic or inorganic base,

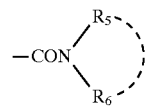

and
a group

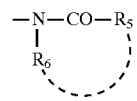

in which $R_5$ and $R_6$, which may be identical to or different from one another, represent H or a linear or branched $C_1$–$C_{10}$ alkyl, linear or branched $C_1$–$C_{10}$ hydroxy- or polyhydroxyalkyl, linear or branched $C_1$–$C_{10}$ ($C_1$–$C_5$ alkoxy)alkyl or linear or branched $C_1$–$C_{10}$ hydroxy- or polyhydroxy($C_1$–$C_5$ alkoxy)alkyl group, or $R_5$ and $R_6$ together form a $C_4$–$C_8$ alkylene, $C_4$–$C_8$ hydroxyalkylene, or $C_4$–$C_8$ polyhydroxyalkylene group having a linear or branched chain which is optionally interrupted by one or more atoms selected from S, O, P and N, so that $R_5$ and $R_6$, with the nitrogen atom to which they are linked, form a 5- to 12-membered nitrogenous heterocycle optionally substituted with one or more hydroxyl groups or $C_1$–$C_4$ hydroxy- or polyhydroxyalkyl groups having a linear or branched chain and optionally containing one or more additional hetero atoms selected from S, O, P and N, $R_4$ represents a group selected from the group consisting of $R_3$ and a group of formula Q—$B_4$, Q being as defined above and $B_4$ representing a group:

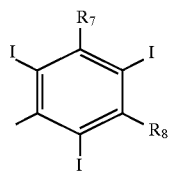

in which $R_7$ and $R_8$, which may be identical to or different from one another, represent $R_3$, the groups $B_3$, which may be identical to or different from one another, are selected from the group consisting of:

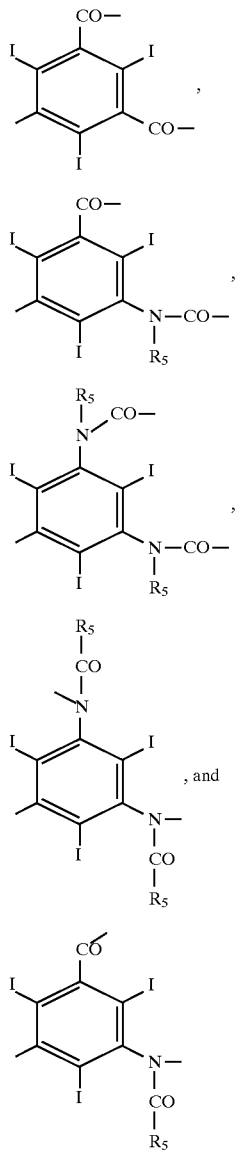

in which R₅ has the meanings given above.

2. Polyiodinated compounds of formula I:

$$A—(X)_m \quad (I)$$

with a molecular weight above 2,000 and below 50,000 in which: A represents the residue of a polyfunctional molecule containing either a central tri- or tetrasubstituted carbon atom, a central trisubstituted phosphorus or nitrogen atom or a trisubstituted

group and/or at least one aromatic or non-aromatic carbocycle optionally containing one or more iodine atoms, or at least one aromatic or non-aromatic heterocycle containing from 1 to 4 hetero atoms selected from the group consisting of O, S, N and P, to which residue are bound m groups X via m groups selected from the group consisting of —CO—,

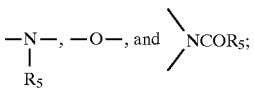

the groups X, which may be identical to or different from one another, represent the groups:

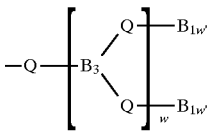

with w, w', Q, B₁ and B₃ as defined in claim 1, and m represents an integer from 2 to 12.

3. Polyiodinated compounds of formula I:

$$A—(X)_m \quad (I)$$

with a molecular weight above 2,000 and below 50,000, in which: A represents:

(a) a residue of a polyfunctional molecule containing a central carbon atom, selected from the group consisting of residues of formula $CR_9(R_{10}—Y)_3$ in which $R_9$ represents a hydrogen atom, a $C_1–C_6$ alkyl or $C_5–C_{10}$ aryl group or a group ($R_{10}$—Y), $R_{10}$ being selected from the group consisting of $C_1–C_6$ alkylene, $C_5–C_{10}$ arylene, ($C_1–C_{10}$ alkyl) ($C_5–C_{10}$ arylene) and ($C_5–C_{10}$ aryl) ($C_1–C_6$ alkylene) group, alkylene groups being optionally interrupted by one or more oxygen atoms, and alkyl, alkylene, aryl and arylene groups being optionally substituted with one or more OH groups, Y being selected from the group consisting of an —O—, —CO— group and a group

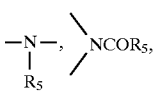

$R_5$ being as defined in claim 1, (b) optionally polycyclic ($C_5–C_{12}$)cycloalkyl residues optionally containing from 1 to 6 iodine atoms and from 2 to 12 identical or different substituents of formula —$R_{11}$—(—Y)$_{\bar{q}}$, q representing an integer from 1 to 3, $R_{11}$ being a single bond or a linear or branched $C_1–C_6$alkylene group optionally substituted with one or more OH groups and/or interrupted by one or more oxygen atoms, and Y being as defined above, (c) monocyclic or bicyclic $C_5–C_{12}$ aromatic hydrocarbon residues optionally containing from 3 to 6 iodine atoms and optionally containing one or more substituents selected from the group consisting of OH, NH₂, $C_1–C_6$ alkyl, $C_1–C_6$ (hydroxy- or polyhydroxy)alkyl, COOH, COOR₁₁, —CO—NHR₁₂ and —NR₆COR₅, R₁₂ representing $C_1–C_4$ alkyl group and containing from 2 to 12 substituents of formula —$R_{11}$—(—Y)—$_{\bar{q}}$, q and $R_{11}$ being as defined above and Y representing a group selected from the group consisting of —O—, —CO—,

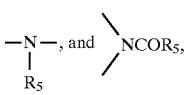

(d) optionally aromatic monocyclic or bicyclic, heterocyclic residue containing from 5 to 10 ring-members comprising 1 to 4 hetero atoms selected from the group consisting of O, S, N and P, optionally substituted with 3 to 6 identical or different substituents selected from the group consisting of =O, and containing from 3 to 12 substituents of the formula $-R_{11}-(-Y)_q$, (e) optionally cyclic residues containing from 2 to 18 aromatic or heterocyclic ring-systems as defined above, linked to one another through groups $-R_{11}-$, $-OR_{11}-$, $R_{11}$ being as defined above, this residue containing from 3 to 12 substituents of formula $-R_{11}-(-Y)_q$, $R_{11}$, Y and q being as defined above, the groups X, which may be identical or different, represent the groups:

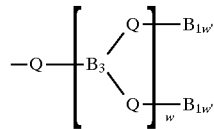

and $w=\Sigma_0^n 2^n$ and $w'=2^n$, n representing an integer from 0 to 4, m represents an integer from 2 to 12, $B_3$ being defined as in claim 1, the groups Q, which may be identical to or different from one another, represent a single bond or a group selected from the group consisting of:

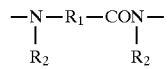
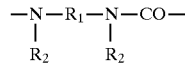
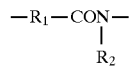
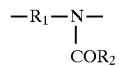
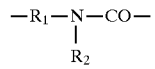
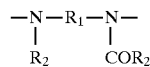
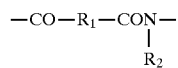
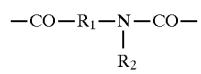
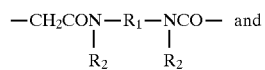
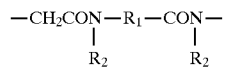

in which:
$R_1$ is selected from the group consisting of a single bond, an alkylene group having a linear or branched $C_1$–$C_{10}$ chain, a hydroxy- or polyhydroxyalkylene group having a linear or branched $C_1$–$C_{10}$ chain, a ($C_1$–$C_5$ alkoxy)alkylene group having a linear or branched $C_1$–$C_{10}$ chain and a hydroxy- or polyhydroxy-($C_1$–$C_5$ alkoxy)alkylene group having a linear or branched chain, the alkylene chain being optionally interrupted by one or more oxygen atoms, and $R_2$ is selected from H, the group consisting of an alkyl group having a linear or branched $C_1$–$C_{10}$ chain, a hydroxy- or polyhydroxyalkyl group having a linear or branched $C_1$–$C_{10}$ chain, a ($C_1$–$C_5$ alkoxy)alkyl group having a linear or branched $C_1$–$C_{10}$ chain and a hydroxy- or polyhydroxy ($C_1$–$C_5$ alkoxy)alkyl group having a linear or branched chain; the groups $B_1$, which may be identical to or different from one another, represent the residue of an aromatic group containing at least three iodine atoms of formula:

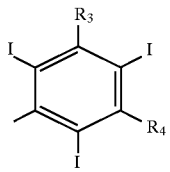

in which
$R_3$ is selected from the group consisting of
—COO⁻ M⁺ with M⁺ representing H⁺ or a physiologically acceptable cation of an organic or inorganic base,
a group

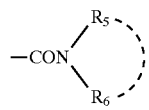

and
a group

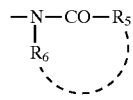

in which $R_5$ and $R_6$, which may be identical to or different from one another, represent H or a liner or branched $C_1$–$C_{10}$ alkyl, linear or branched $C_1$–$C_{10}$(hydroxy- or polyhydroxy) alkyl, linear or branched $C_1$–$C_{10}$ ($C_1$–$C_5$ alkoxy)alkyl or linear or branched $C_1$–$C_{10}$ hydroxy- or polyhydroxy($C_1$–$C_5$ alkoxy)alkyl group, or $R_5$ and $R_6$ together form a $C_4$–$C_8$ alkylene, $C_4$–$C_8$ hydroxyalkylene or $C_4$–$C_8$ polyhydroxyalkylene group having a linear or branched chain which is optionally interrupted by one or more atoms selected from the group consisting of S, O, P and N, so that $R_5$ and $R_6$, with the nitrogen atom to which they are linked, form a 5- to 12-membered nitrogenous heterocycle optionally substituted with one or more hydroxyl groups or $C_1$–$C_4$ (hydroxy- or polyhydroxy)alkyl groups having a linear or branched chain and optionally containing one or more additional hetero atoms selected from S, O, P and N, $R_4$ represents a group selected from the group consisting of $R_3$ and the groups of formula Q—$B_4$, Q being as defined above and $B_4$ representing a group

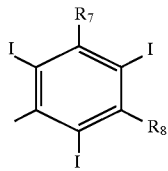

in which $R_7$ and $R_8$, which may be identical to or different from one another, represent $R_3$ as defined above.

4. Polyiodinated compounds according to claim 3, characterized in that A is selected from the group consisting of (a) residues of formula $C(R_{10}-Y)_{\overline{4}}R_{10}$ representing a methylene, phenylene or phenylmethylene group or a $-CH_2-O-CH_2-$ or $-CH_2-O-(CH_2)_2-$ group, and Y being as defined in claim 3;

(b) cycloalkyl residues selected from cyclohexyl and adamantyl substituted with 3 or 4 substituents q $R_{11}-(-Y)_{\overline{q}}$ as defined in claim 3;

(c) phenyl groups optionally substituted with 3 or 4 iodine atoms or biphenyl groups optionally substituted with 4 to 6 iodine atoms and optionally containing from 3 to 6 substituents of formula $R_{11}-(-Y)_{\overline{q}}$, q, $R_{11}$ and Y being as defined in claim 3;

(d) heterocyclic residues consisting of a 2,4,6-trioxo-1,3,5-triazine group substituted on the nitrogen atoms with 3 substituents of formula $-R_{11}-(-Y)_{\overline{q}}$ as defined in claim 3;

(e) macrocyclic residues consisting of 6 to 8 phenyl residues each substituted with one or more substituents selected from the group consisting of OH, $NH_2$, $C_1$-$C_6$ alkyl, $C_1$-$C_6$ hydroxy- or polyhydroxyalkyl, COOH, $COOR_{11}$, $-CO-NHR_{12}$ and $-NR_6COR_5$, $R_{11}$ representing a $C_1$-$C_4$ alkyl group, and one or more groups of the formula $R_{11}-(-Y)_{\overline{q}}$ as defined above with q=1, the phenyl residues being linked to one another through a methylene group, or a cyclodextrin composed of 6 to 8 glucosyl residues linked to one another through a glycosidic linkage, one or more OH groups of said glucosyl residues being optionally substituted with a carboxymethyl residue, one or more OH groups of said glucosyl residues being replaced by an $-O-$ group, or macrocylic residue containing more than one nitrogen or a derivative of a polyaminocarboxylic acid residue.

5. Polyiodinated compounds according to claim 3, in which the groups $B_1$ are selected from the group consisting of:

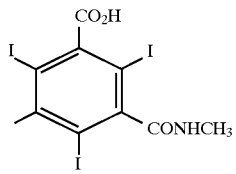

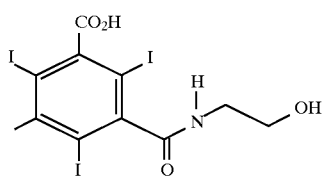

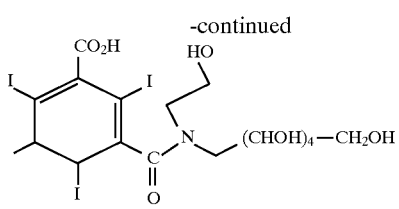

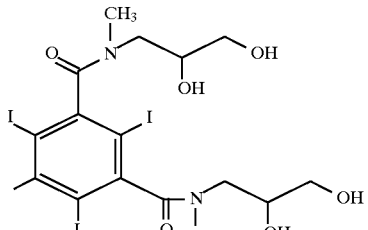

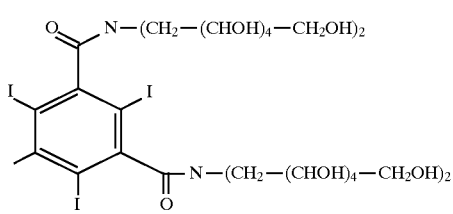

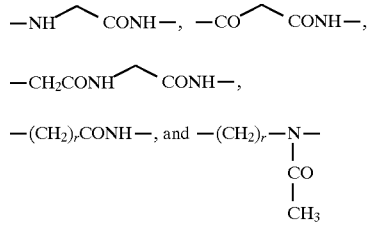

6. Polyiodinated compounds according to claim 3, in which the group Q is selected from the group consisting of:

$-NH\frown CONH-$, $-CO\frown CONH-$, $-CH_2CONH\frown CONH-$, $-(CH_2)_rCONH-$, and $-(CH_2)_r-N-$
$\phantom{-(CH_2)_rCONH-, and -(CH_2)_r-N}|$
$\phantom{-(CH_2)_rCONH-, and -(CH_2)_r-N}CO$
$\phantom{-(CH_2)_rCONH-, and -(CH_2)_r-N}|$
$\phantom{-(CH_2)_rCONH-, and -(CH_2)_r-N}CH_3$ r being an integer from 1 to 5.

7. Polyiodinated compounds according to claim 3, in which $R_3$ is selected from the group consisting of:

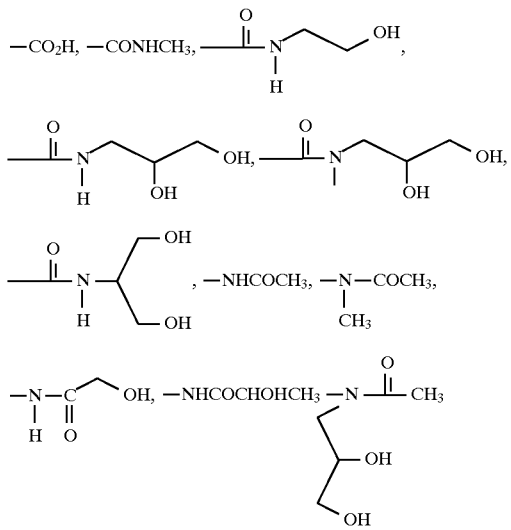

-continued

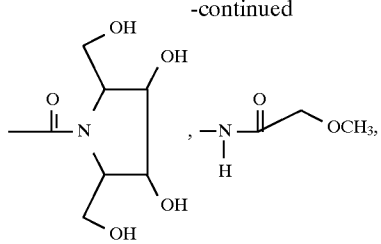

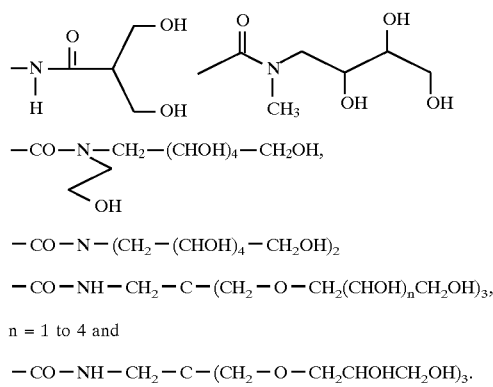

$-CO-N-(CH_2-(CHOH)_4-CH_2OH)_2$ $-CO-NH-CH_2-C-(CH_2-O-CH_2(CHOH)_nCH_2OH)_3$, n = 1 to 4 and $-CO-NH-CH_2-C-(CH_2-O-CH_2CHOHCH_2OH)_3$.

8. Polyiodinated compounds according to claim 3, characterized in that they have the formula V:

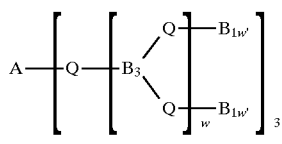

$w=\Sigma_0^n 2^n$ and $w'=2^n$ (n representing an integer from 0 to 4) in which A is defined as in claim 3, Q represents a group

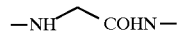

and $B_3$ represents a group:

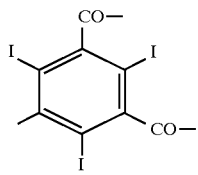

and $B_1$ represents a group

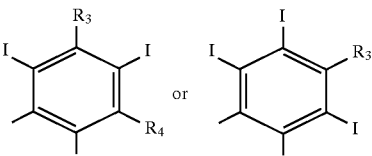

in which
$R_3$ and $R_4$ are selected from the group consisting of $CO^-_2$ $M^+$ $-CO-N-CH_2-(CHOH)_4-CH_2OH$,

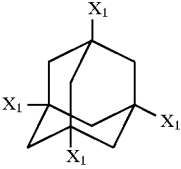

$-CO-N-(CH_2-(CHOH)_4-CH_2OH)2$

9. Polyiodinated compounds characterized in that they are selected from the group consisting of:

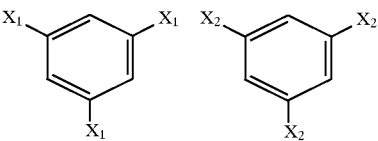

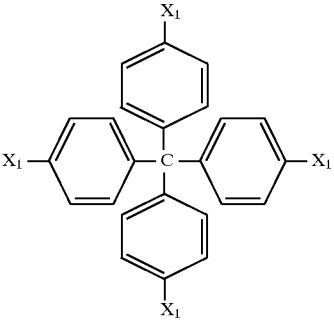

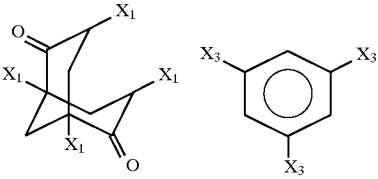

with:

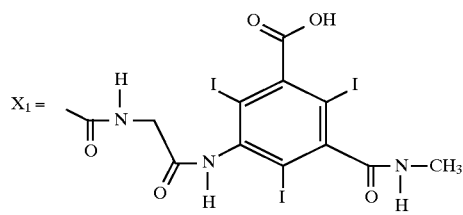
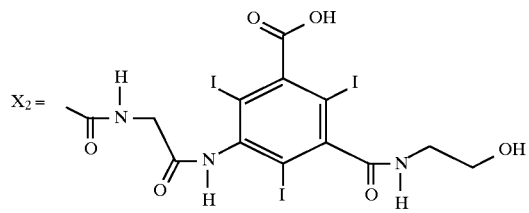
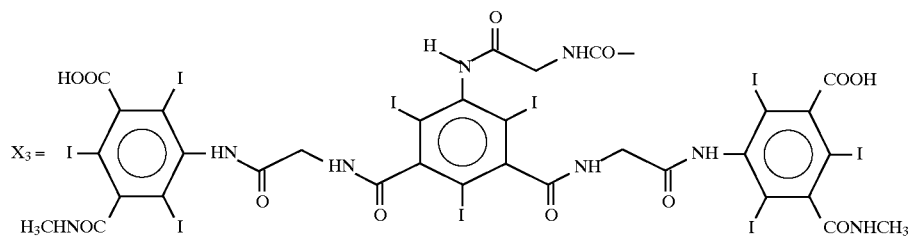
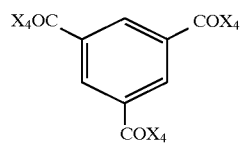
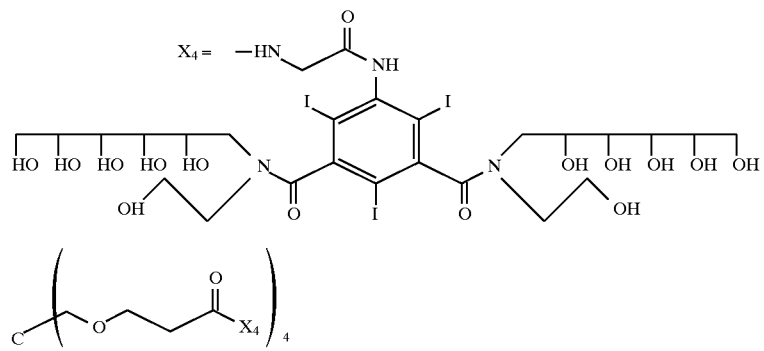
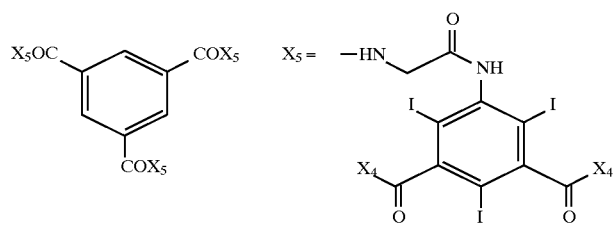
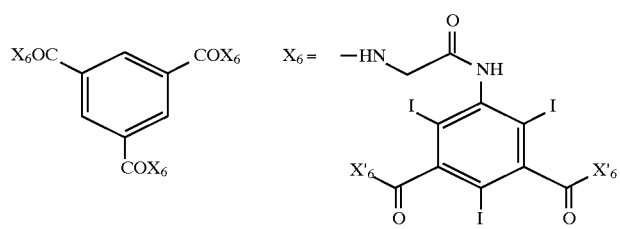

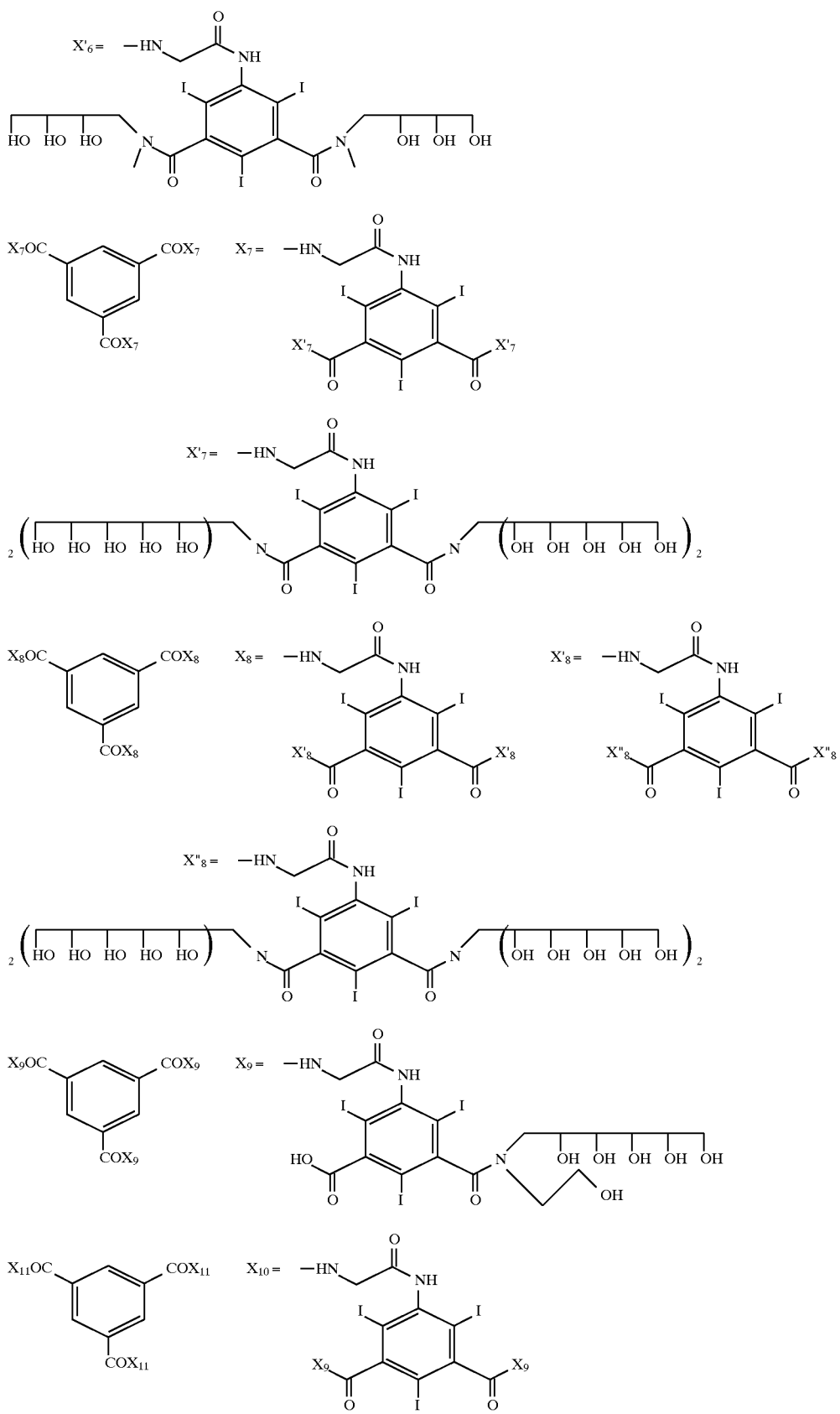

-continued

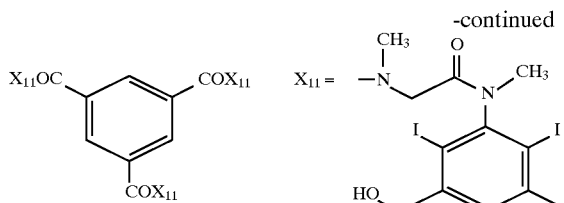 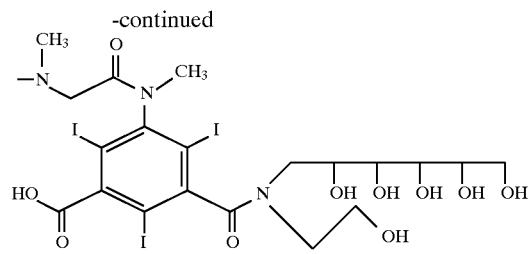

10. Contrast medium, characterized in that it contains at least one compound according to claim 3.

11. Contrast medium according to claim 10, characterized in that it comprises an aqueous solution of the compound or compounds.

12. Polyiodinated compounds of generic formula I:

A—(X)$_m$  (I)

in which:

A represents the residue of a polyfunctional molecule containing either a central tri- or tetrasubstituted carbon atom, a central trisubstituted phosphorus or nitrogen atom or a trisubstituted

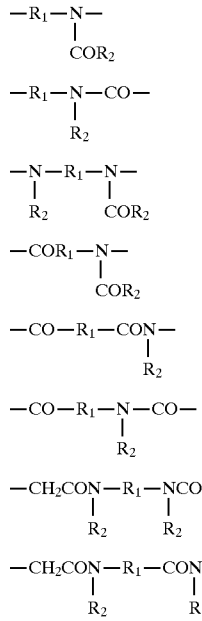

group and/or at least one aromatic or non-aromatic carbocycle optionally containing one or more iodine atoms, or at least one aromatic or non-aromatic heterocycle containing from 1 to 4 hetero atoms selected from O, S, N and P, to which residues are bound m groups X via functional groups selected from the group consisting of —CO—,

—O—, and >NCOR$_5$; the groups X, which may be identical to or different from one another are selected from the group consisting of the group consisting of:

—Q—B$_1$  (A),

—Q—A$_1$—(Q—B$_1$)$_{m'}$  (B), m' representing from 2 to 11; and

—Q—B$_2$—Q—B$_1$  (C)

m represents an integer from 3 to 12, the groups Q, which may be identical or different from one another, represent a single bond or a group selected from:

-continued

in which:

R$_1$ is selected from the group consisting of an alkylene group having a linear or branched C$_1$–C$_{10}$ chain, a hydroxy- or polyhydroxyalkylene group having a linear or branched C$_1$–C$_{10}$ chain, a (C$_1$–C$_5$ alkoxy)alkylene group having a linear or branched C$_1$–C$_{10}$ chain, a hydroxy- or polyhydroxy(C$_1$–C$_5$ alkoxy)alkylene group having a linear or branched chain, and a single bond, and the R$_2$ groups identical or different being selected from the group consisting of H, an alkyl group having a linear or branched C$_1$–C$_{10}$ chain, a hydroxy- or polyhydroxyalkyl group having a linear or branched C$_1$–C$_{10}$ chain, a (C$_1$–C$_5$ alkoxy)alkyl group having a linear or branched C$_1$–C$_{10}$ chain and a hydroxy- or polyhydroxy(C$_1$–C$_5$ alkoxy)alkyl group having a linear or branched chain;

the groups B$_1$, which may be identical to or different from one another, represent the residue of an aromatic group containing at least three iodine atoms, of formula:

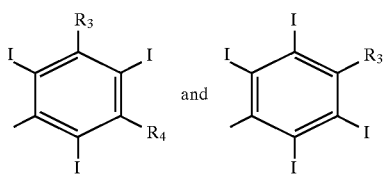

in which $R_3$ is selected from the group consisting of:
a group —COO⁻ M⁺ with M⁺ representing H⁺ or a physiologically acceptable cation of an organic or inorganic base,
a group

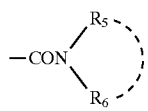

and
group

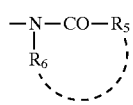

in which $R_5$ and $R_6$, which may be identical to or different from one another, represent H or a linear or branched $C_1$–$C_{10}$ alkyl, linear or branched $C_1$–$C_{10}$ hydroxy- or polyhydroxyalkyl, linear or branched $C_1$–$C_{10}$ ($C_1$–$C_5$ alkoxy)alkyl or linear or branched $C_1$–$C_{10}$ hydroxy- or polyhydroxy($C_1$–$C_5$ alkoxy) alkyl group, or $R_5$ and $R_6$ together form a $C_4$–$C_8$ alkylene, $C_4$–$C_8$ hydroxyalkylene or $C_4$–$C_8$ polyhydroxyalkylene group having a linear or branched chain which is optionally interrupted by one or more atoms selected from the group consisting of S, O, P and N, so that $R_5$ and $R_6$, with the nitrogen atom to which they are linked, form a 5- to 12-membered nitrogenous heterocycle optionally substituted with one or more hydroxyl groups or $C_1$–$C_4$ hydroxy- or polyhydroxyalkyl groups having a linear or branched chain and optionally containing one or more additional hetero atoms selected from the group consisting of S, O, P and N, $R_4$ represents a group selected from the group consisting of $R_3$ and a group of formula Q—$B_4$, Q being as defined above and $B_4$ representing a group:

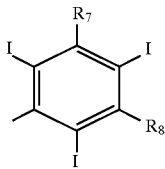

in which $R_7$ and $R_8$, which may be identical to or different from one another, represent $R_3$, $A_1$ is selected from the group consisting of groups A, with the proviso that at least one group —CO—,

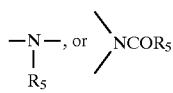

or >NCOR$_5$ is replaced by a single bond, $B_2$ is selected from the group consisting:

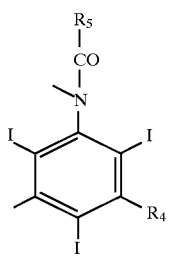

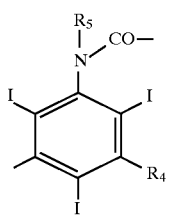

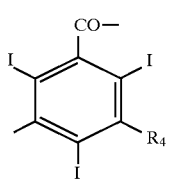

in which $R_4$ and $R_5$ have the meanings given above, with the proviso that said compounds contain a zero overall electrical charge or at least two anionic charges when A–(X)$_m$=A (QB$_1$)$_3$, and that said compounds have a molecular weight above 2,000 and below 50,000 and a molecular concentration of iodine greater than 20%.

13. Polyiodinated compounds according to claim 1, in which the groups $B_1$ are selected from the group consisting of:

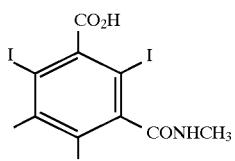

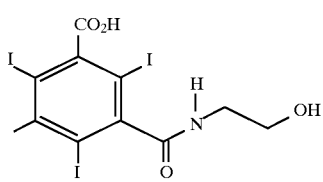

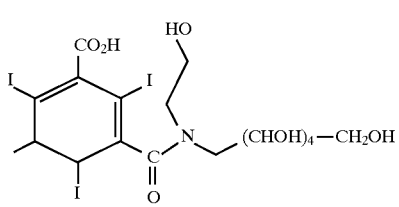

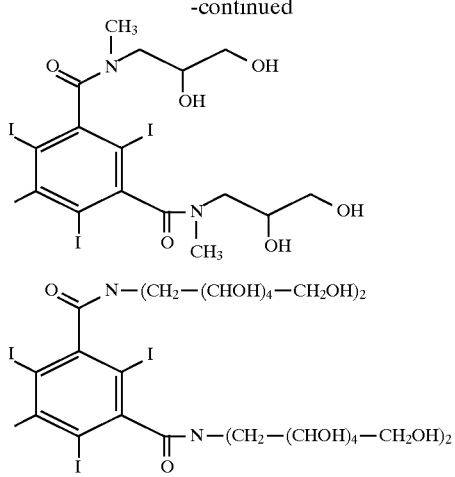

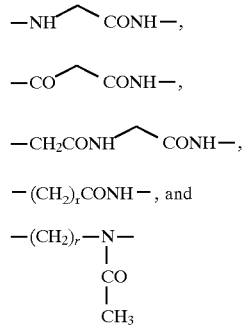

14. Polyiodinated compounds according to claim 1, in which the group Q is selected from the group consisting of:

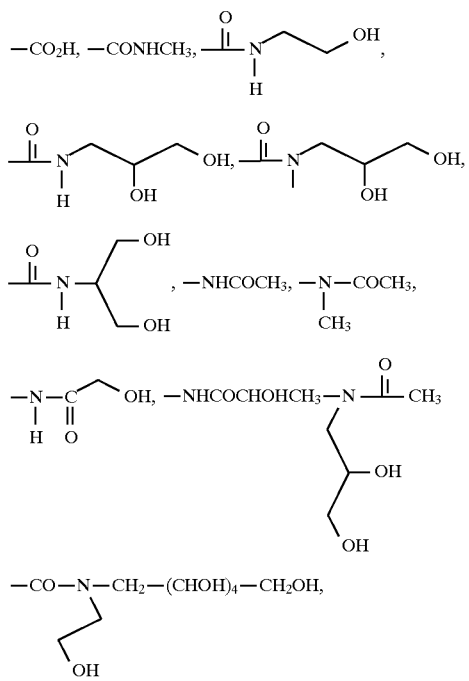

r being an integer from 1 to 5.

15. Polyiodinated compounds according to claim 1, in which $R_3$ is selected from the group consisting of:

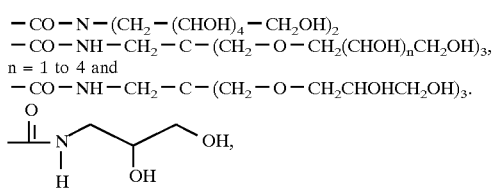

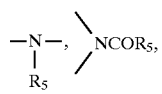

16. Contrast medium, characterized in that it contains at least one compound according to claim 1.

17. Contrast medium, characterized in that it contains at least one compound according to claim 1.

18. Polyiodinated compounds of formula I:

$$A\text{-}(X)_m \qquad (I)$$

with a molecular weight above 2,000 and below 50,000, in which: A represents:

(a) a residue of a polyfunctional molecule containing a central carbon atom, selected from the group consisting of residues of formula $CR_9(R_{10}\text{—}Y)_3$ in which $R_9$ represents a hydrogen atom, a $C_1\text{–}C_6$ alkyl or $C_5\text{–}C_{10}$ aryl group or a group $(R_{10}\text{—}Y)$, $R_{10}$ being selected from the group consisting of $C_1\text{–}C_6$ alkylene, $C_5\text{–}C_{10}$ arylene, $(C_1\text{–}C_{10}$ alkyl) $(C_5\text{–}C_{10}$ arylene) and $(C_5\text{–}C_{10}$ aryl) $(C_1\text{–}C_6$ alkylene) group, alkylene groups being optionally interrupted by one or more oxygen atoms, and alkyl, alkylene, aryl and arylene groups being optionally substituted with one or more OH groups, Y being selected from the group consisting of an —O—, —CO— group and a group $$-\underset{R_5}{N}-, \quad \diagup{NCOR_5},$$

$R_5$ being as defined in claim 1, (b) optionally polycyclic $(C_5\text{–}C_{12})$cycloalkyl residues optionally containing from 1 to 6 iodine atoms and from 2 to 12 identical or different substituents of formula —$R_{11}$—(—Y—)$_q$, a representing an integer from 1 to 3, $R_{11}$ being a single bond or a linear or branched $C_1\text{–}C_6$ alkylene group optionally substituted with one or more OH groups and/or interrupted by one or more oxygen atoms, and Y being as defined above, (c) monocyclic or bicyclic $C_5\text{–}C_{12}$ aromatic hydrocarbon residues optionally containing from 3 to 6 iodine atoms and optionally containing one or more substituents selected from the group consisting of OH, $NH_2$, $C_1\text{–}C_6$ alkyl, $C_1\text{–}C_6$ (hydroxy- or polyhydroxy)alkyl, COOH, $COOR_{11}$, —CO—$NHR_{12}$ and —$NR_6COR_5$, $R_{12}$ representing $C_1\text{–}C_4$ alkyl group and containing from 2 to 12 substituents of formula —$R_{11}$—(—Y—)$_q$, q and $R_{11}$ being as defined above and Y representing a group selected from the group consisting of —O—, —CO—,

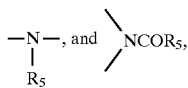

(d) optionally aromatic monocyclic or bicyclic, heterocyclic residue containing from 5 to 10 ring-members comprising 1 to 4 hetero atoms selected from the group consisting of O, S, N and P, optionally substituted with 3 to 6 identical or different substituents selected from the group consisting of =O, and containing from 3 to 12 substituents of formula the $-R_{11}-(-Y-)_{\overline{q}}$, q being defined above, (e) optionally cyclic residues containing from 2 to 18 aromatic or heterocyclic ring-systems as defined above, linked to one another through groups $-R_{11}-$, $-OR_{11}-$, $R_{11}$ being as defined above, this residue containing from 3 to 12 substituents of formula $-R_{11}-(-Y-)_{\overline{q}}$, $R_{11}$, Y and q being as defined above, the groups X, which may be identical or different, represent the groups:

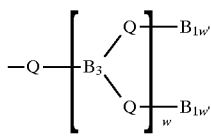

and $w=\Sigma_0^n 2^n$ and $W'=2^n$, n representing an integer from 0 to 4, m represents an integer from 2 to 12, $B_3$ being defined as in claim 1, the groups Q, which may be identical to or different from one another, represent a single bond or a group selected from the group consisting of:

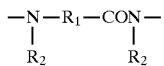

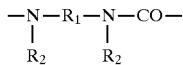

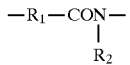

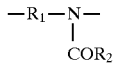

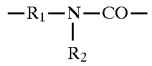

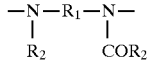

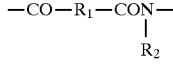

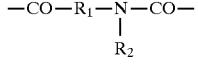

-continued

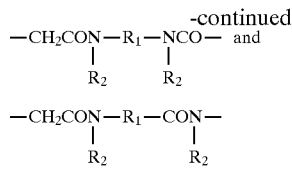

in which:
$R_1$ is selected from the group consisting of a single bond, an alkylene group having a linear or branched $C_1-C_{10}$ chain, a hydroxy- or polyhydroxyalkylene group having a linear or branched $C_1-C_{10}$ chain, a ($C_1-C_5$ alkoxy)alkylene group having a linear or branched $C_1-C_{10}$ chain and a hydroxy- or polyhydroxy-($C_1-C_5$ alkoxy)alkylene group having a linear or branched chain, the alkylene chain being optionally interrupted by 1 to 4 oxygen atoms, and $R_2$ is selected from H, the group consisting of an alkyl group having a linear or branched $C_1-C_{10}$ chain, a hydroxy- or polyhydroxyalkyl group having a linear or branched $C_1-C_{10}$ chain, a ($C_1-C_5$ alkoxy)alkyl group having a linear or branched $C_1-C_{10}$ chain and a hydroxy- or polyhydroxy ($C_1-C_5$ alkoxy)alkyl group having a linear or branched chain; the groups $B_1$, which may be identical to or different from one another, represent the residue of an aromatic group containing at least three iodine atoms of formula:

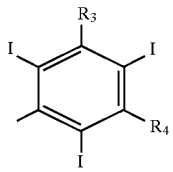

in which
$R_3$ is selected from the group consisting of $-COO^- M^+$ with $M^+$ representing $H^+$ or a physiologically acceptable cation of an organic or inorganic base,
a group

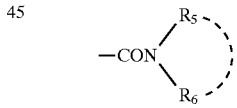

and
a group

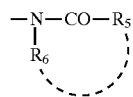

in which $R_5$ and $R_6$, which may be identical to or different from one another, represent H or a liner or branched $C_1-C_{10}$ alkyl, linear or branched $C_1-C_{10}$(hydroxy- or polyhydroxy) alkyl, linear or branched $C_1-C_{10}$ ($C_1-C_5$ alkoxy)alkyl or linear or branched $C_1-C_{10}$ hydroxy- or polyhydroxy($C_1-C_5$ alkoxy)alkyl group,
or $R_5$ and $R_6$ together form a $C_4-C_8$ alkylene, $C_4-C_8$ hydroxyalkylene or $C_4-C_8$ polyhydroxyalkylene group having a linear or branched chain which is optionally interrupted by one or more atoms selected from the group consisting of S, O, P and N, so that $R_5$ and $R_6$, with the nitrogen atom to which they are linked, form a 5- to 12-membered nitrogenous heterocycle optionally substituted with one or more hydroxyl groups or $C_1$–$C_4$ (hydroxy- or polyhydroxy)alkyl groups having a linear or branched chain and optionally containing one or more additional hetero atoms selected from S, O, P and N, $R_4$ represents a group selected from the group consisting of $R_3$ and the groups of formula Q—$B_4$, Q being as defined above and $B_4$ representing a group

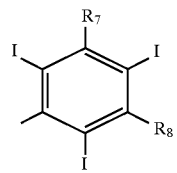

in which $R_7$ and $R_8$, which may be identical to or different from one another, represent $R_3$ as defined above.

* * * * *